(12) United States Patent
Moffett et al.

(10) Patent No.: US 12,054,531 B2
(45) Date of Patent: Aug. 6, 2024

(54) RECOMBINANT CELL SURFACE MARKERS

(71) Applicant: Lyell Immunopharma, Inc., South San Francisco, CA (US)

(72) Inventors: Howell Franklin Moffett, Seattle, WA (US); Marc Joseph Lajoie, Seattle, WA (US); Scott Edward Boyken, Seattle, WA (US)

(73) Assignee: LYELL IMMUNOPHARMA, INC., South San Francisco, CA (US)

( * ) Notice: Subject to any disclaimer, the term of this patent is extended or adjusted under 35 U.S.C. 154(b) by 306 days.

(21) Appl. No.: 17/207,523

(22) Filed: Mar. 19, 2021

(65) Prior Publication Data

US 2021/0309717 A1 Oct. 7, 2021

Related U.S. Application Data

(60) Provisional application No. 63/137,022, filed on Jan. 13, 2021, provisional application No. 62/992,806, filed on Mar. 20, 2020.

(51) Int. Cl.
| | |
|---|---|
| *C07K 14/71* | (2006.01) |
| *A61K 35/17* | (2015.01) |
| *C07K 14/535* | (2006.01) |
| *C07K 14/705* | (2006.01) |
| *C07K 14/725* | (2006.01) |
| *C07K 16/28* | (2006.01) |
| *A61K 38/00* | (2006.01) |

(52) U.S. Cl.
CPC .............. *C07K 14/71* (2013.01); *A61K 35/17* (2013.01); *C07K 14/535* (2013.01); *C07K 14/7051* (2013.01); *C07K 14/70596* (2013.01); *C07K 16/2863* (2013.01); *A61K 38/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 6,790,614 B1 | 9/2004 | Pippig et al. |
| 8,802,374 B2 | 8/2014 | Jensen |
| 9,580,685 B2 | 2/2017 | Jensen |
| 9,758,586 B2 | 9/2017 | Rader et al. |
| 10,100,281 B2 | 10/2018 | Jensen |
| 11,014,989 B2 | 5/2021 | Smith et al. |
| 11,155,783 B2 | 10/2021 | Jensen |
| 11,400,117 B2 | 8/2022 | MacKall et al. |
| 2017/0044235 A1 | 2/2017 | Listek et al. |
| 2017/0051308 A1* | 2/2017 | Morgan ................. A61P 43/00 |
| 2018/0000914 A1 | 1/2018 | Valton et al. |
| 2018/0002427 A1 | 1/2018 | Smith et al. |
| 2019/0277844 A1* | 9/2019 | Guo ...................... A61K 31/713 |
| 2020/0040058 A1 | 2/2020 | Hudecek et al. |
| 2020/0155597 A1 | 5/2020 | Crane et al. |
| 2021/0332326 A1 | 10/2021 | Vodnala |
| 2021/0380658 A1 | 12/2021 | Lajoie et al. |
| 2022/0307039 A1 | 9/2022 | Park et al. |
| 2023/0022654 A1 | 1/2023 | Park et al. |

FOREIGN PATENT DOCUMENTS

| | | | |
|---|---|---|---|
| EP | 2496698 B1 | 1/2019 | |
| EP | 2814846 B1 | 1/2020 | |
| EP | 3129405 B1 | 2/2021 | |
| WO | 2011/056894 A2 | 5/2011 | |
| WO | 2012/075158 A1 | 6/2012 | |
| WO | WO-2013123061 A1 * | 8/2013 | ............ A61K 35/17 |
| WO | 2017/120997 A1 | 7/2017 | |
| WO | 2017/120998 A1 | 7/2017 | |
| WO | 2018/006880 A1 | 1/2018 | |
| WO | 2018/006881 A1 | 1/2018 | |
| WO | 2018/137293 A1 | 8/2018 | |
| WO | 2018/137294 A1 | 8/2018 | |
| WO | 2019/070856 A1 | 4/2019 | |
| WO | 2019/072824 A1 | 4/2019 | |
| WO | 2019/118902 A2 | 6/2019 | |
| WO | 2019/149743 A1 | 8/2019 | |
| WO | 2019/223226 A1 | 11/2019 | |
| WO | 2020/014366 A1 | 1/2020 | |
| WO | 2020/018691 A1 | 1/2020 | |
| WO | 2020/033272 A1 | 2/2020 | |
| WO | 2020/037178 A1 | 2/2020 | |
| WO | 2020/037181 A1 | 2/2020 | |
| WO | 2020/069508 A1 | 4/2020 | |
| WO | 2020/070289 A1 | 4/2020 | |
| WO | 2020/083282 A1 | 4/2020 | |
| WO | 2020/088631 A1 | 5/2020 | |

(Continued)

OTHER PUBLICATIONS

Li et al., "Structural basis for inhibition of the epidermal growth factor receptor by cetuximab" Cancer Cell, Apr. 2005, 7:301-11.
Paszkiewicz et al., "Targeted antibody-mediated depletion of murine CD19 CAR T cells permanently reverses B cell aplasia" J Clinical Investigation, Nov. 2016, 126(11): 4262-72.
Wang et al., "Atransgene-encoded cell surface polypeptide for selection, in vivo tracking, and ablation of engineered cells" Blood, Aug. 4, 2011, 118(5): 1255-63.

(Continued)

*Primary Examiner* — Meera Natarajan
*Assistant Examiner* — Cheom-Gil Cheong
(74) *Attorney, Agent, or Firm* — STEPTOE LLP; Z. Ying Li; Debashree Chatterjee

(57) ABSTRACT

The present disclosure relates to EGFR-derived polypeptides containing short juxtamembrane sequences, nucleic acids encoding them, and methods of using them to improve cell surface expression of truncated EGFR markers.

28 Claims, 19 Drawing Sheets

Specification includes a Sequence Listing.

(56) References Cited

FOREIGN PATENT DOCUMENTS

| WO | 2020/187016 A1 | 9/2020 |
| WO | 2021/222479 A9 | 11/2021 |
| WO | 2021/231655 A1 | 11/2021 |
| WO | 2022/182890 A1 | 9/2022 |
| WO | 2022/182891 A1 | 9/2022 |
| WO | 2022/182915 A1 | 9/2022 |

OTHER PUBLICATIONS

U.S. Appl. No. 17/318,996, filed May 12, 2021, Marc Joseph Lajoie.
U.S. Appl. No. 17/680,024, filed Feb. 24, 2022, Spencer Park.
U.S. Appl. No. 18/050,414, filed Oct. 27, 2022, Suman Kumar Vodnala.
U.S. Appl. No. 17/679,977, filed Feb. 24, 2022, Spencer Park.
U.S. Appl. No. 18/050,411, filed Oct. 27, 2022, Suman Kumar Vodnala.
U.S. Appl. No. 17/243,566, filed Apr. 28, 2021, Suman Kumar Vodnala.
U.S. Appl. No. 17/850,825, filed Jun. 27, 2022, Crystal Mackall.
Davila et al., "CD19 CAR-Targeted T Cells Induce Long-Term Remission and B Cell Aplasia in an Immunocompetent Mouse Model of B Cell Acute Lymphoblastic Leukemia." PLoS One (2013) 8(4):e61338, 1-14.
Ferguson, "Structure-Based View of Epidermal Growth Factor Receptor Regulation." Annu. Rev. Biophys. (2008) 37:353-73.
Hedger et al., "The juxtamembrane regions of human receptor tyrosine kinases exhibit conserved interaction sites with anionic lipids" Sci Rep. (2015) 5: 9198, 1-10.
Kovacs et al., "A Structural Perspective on the Regulation of the Epidermal Growth Factor Receptor." Annu. Rev. Biochem. (2015) 84:1, 739-764. https://www.annualreviews.org/doi/pdf/10.1146/annurev-biochem-060614-034402.
Liu et al., "Systematic comparison of 2A peptides for cloning multi-genes in a polycistronic vector." Sci Rep. (2017) 7:2193, 1-9.
McLaughlin et al., "An Electrostatic Engine Model for Autoinhibition and Activation of the Epidermal Growth Factor Receptor (EGFR/ErbB) Family." J. Gen. Physiol. (2005) 126:1, 41-53. https://rupress.org/jgp/article-pdf/126/1/41/1220830/jgp126141.pdf.
Sengupta et al., "EGFR Juxtamembrane Domain, Membranes, and Calmodulin: Kinetics of Their Interaction", Biophysical Journal (2009) 96:12, 4887-95.
Yang et al., "Therapeutic Potential and Challenges of Targeting Receptor Tyrosine Kinase ROR1 with Monoclonal Antibodies in B-Cell Malignancies." PLoS One. (2011) 6:e21018, 1-15.

* cited by examiner

Native EGFR with sequences of transmembrane and juxtamembrane domains

```
[S.peptide][Extracellular][Transmembrane 646-668] [Juxtamembrane 669-703]            [Kinase Domain]
(1-24)     (25-645)       IATGMVGALLLLLVVALGIGLFM RRRHIVRKRTLRRLLQERELVEPLTPSGEAPNQAL (704-1210)
                                                  +++    +++  ++    -+-  -       -
```

FIG. 2A

Truncated EGFR test constructs with juxtamembrane domains

| [S.peptide] | [Extracellular] | [Transmembrane] | [Juxtamembrane] |
|---|---|---|---|
| GMCSF | Domain III-IV | IATGMVGALLLLLVVALGIGLFM | * |
| GMCSF | Domain III-IV | IATGMVGALLLLLVVALGIGLFM | RRR* |
| GMCSF | Domain III-IV | IATGMVGALLLLLVVALGIGLFM | RRRHIVRKR* |
| GMCSF | Domain III-IV | IATGMVGALLLLLVVALGIGLFM | RRRSGGGGSGGGGS* |
| GMCSF | Domain III-IV | IATGMVGALLLLLVVALGIGLFM | SGGGGSGGGGS* |

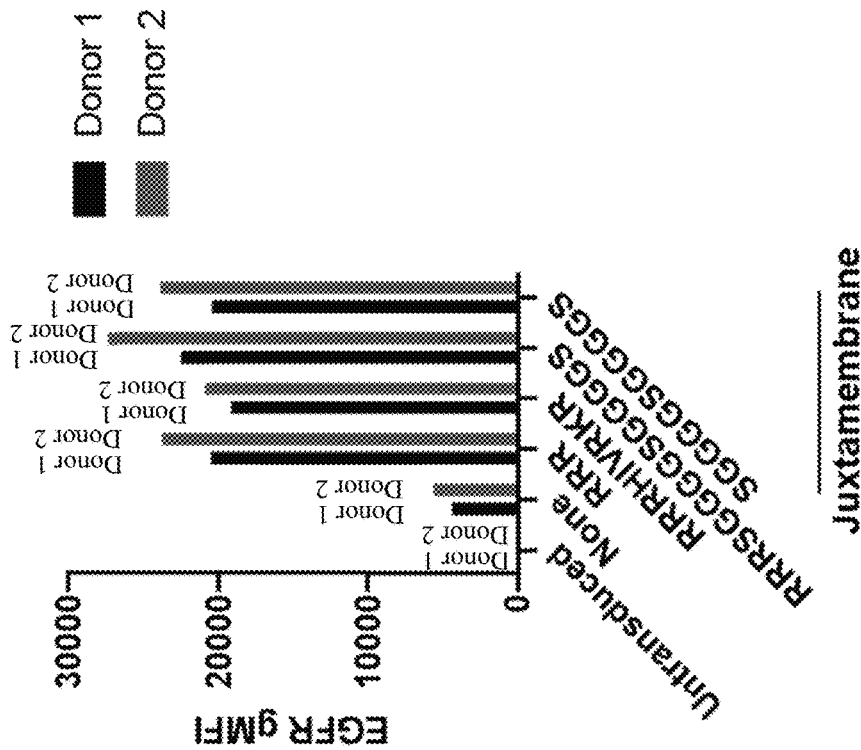
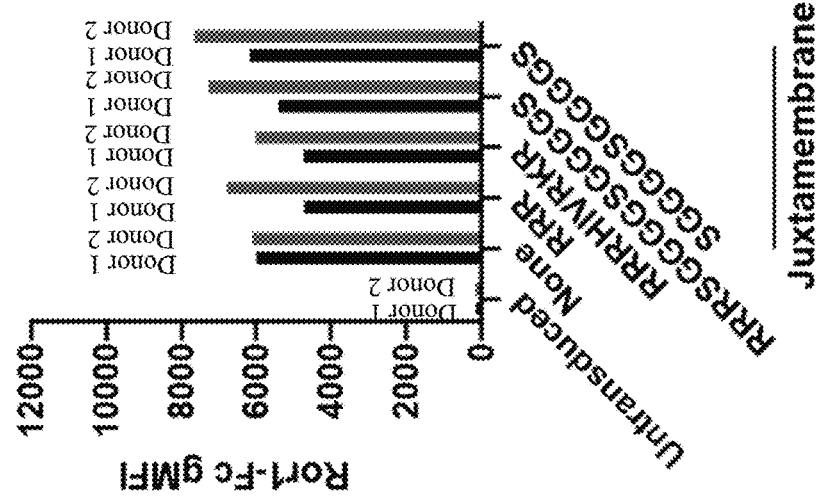
FIG. 3A  FIG. 3B  FIG. 3C

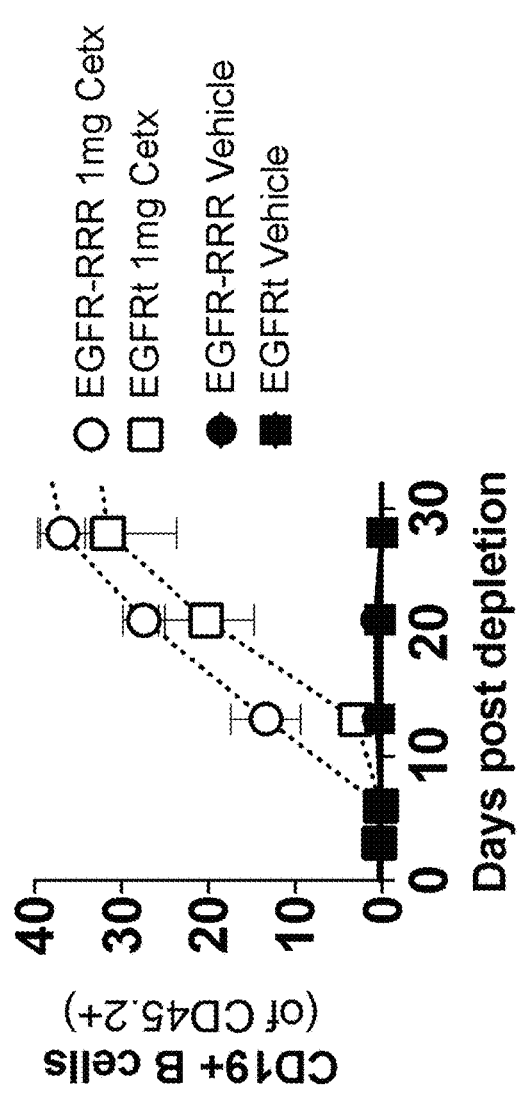 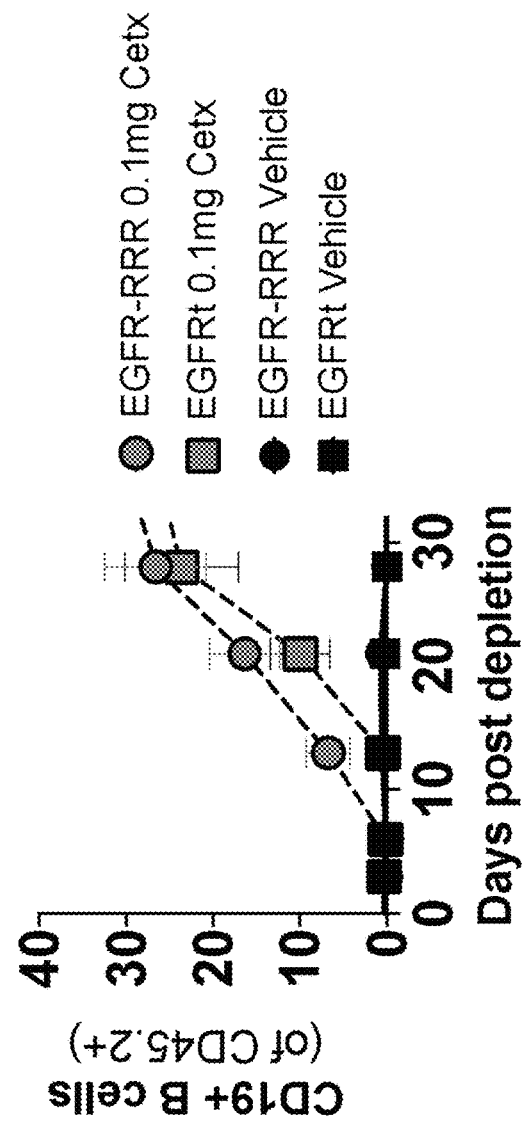
FIG. 13B

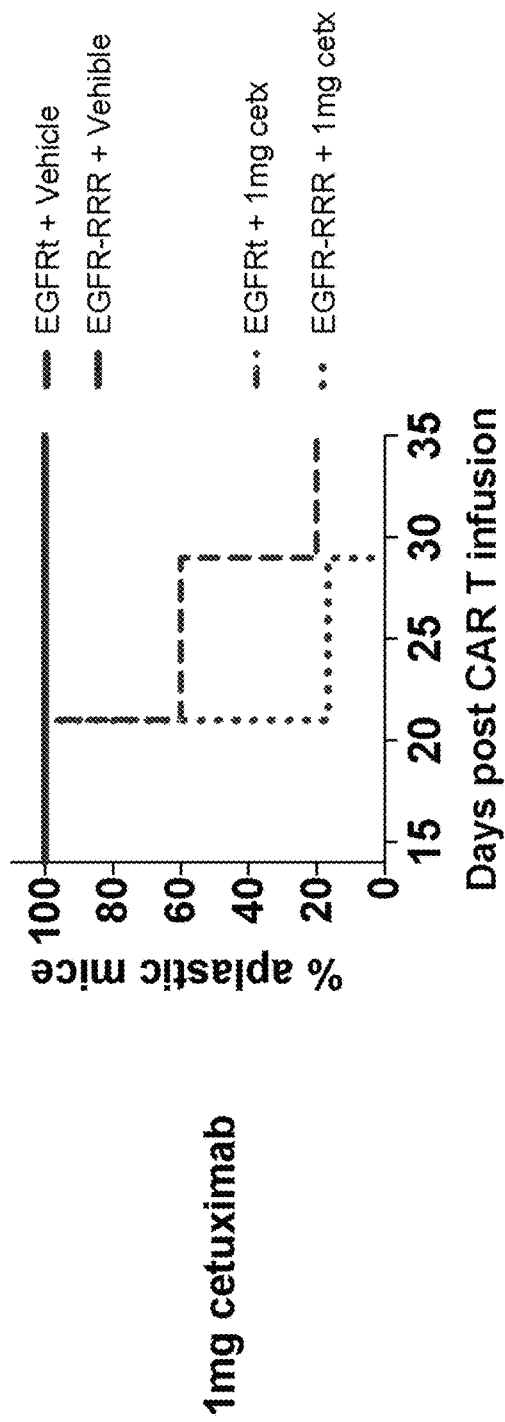
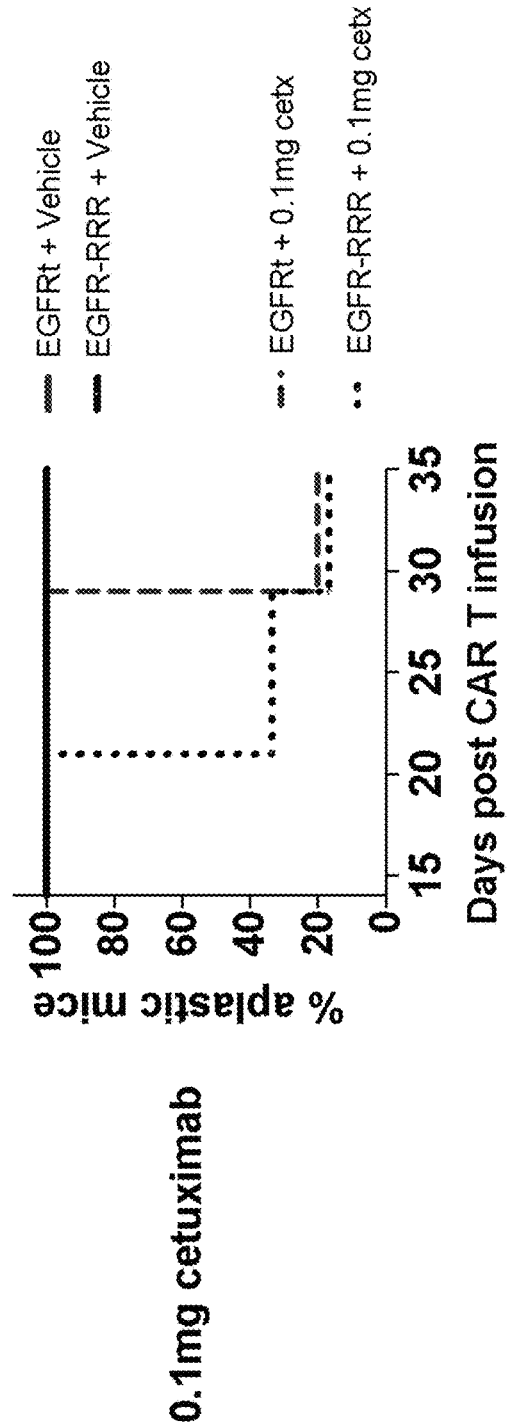
FIG. 13C

ID NO:1.

RECOMBINANT CELL SURFACE MARKERS

CROSS-REFERENCE TO RELATED APPLICATIONS

This application claims priority from U.S. Provisional Application 62/992,806, filed Mar. 20, 2020, and U.S. Provisional Application 63/137,022, filed Jan. 13, 2021. The disclosures of the aforementioned provisional applications are incorporated herein by reference in their entirety.

SEQUENCE LISTING

The instant application contains a Sequence Listing that has been submitted electronically in ASCII format. The Sequence Listing is hereby incorporated by reference in its entirety. The ASCII copy, created on Mar. 19, 2021, is named 026225_US012_SL.txt and is 59,472 bytes in size.

BACKGROUND OF THE INVENTION

The epidermal growth factor family of receptors tyrosine kinases (ErbBs) consists of four members: EGFR/ErbB1/HER1, ErbB2/HER2/Neu, ErbB3/HER3, and ErbB4/HER4 (Wieduwilt and Moasser, *Cell Mol Life Sci.* (2008) 65(10): 1566-84). These receptors are widely expressed in epithelial, mesenchymal, and neuronal tissue and play critical roles in cell proliferation, differentiation, and development (Yano et al., *Anticancer Res.* (2003) 23(5A):3639-50). They are activated by ligands that induce either homo- or hetero-dimerization of the epidermal growth factor receptor (EGFR) homologs. EGFR is a 180 kDa monomeric glycoprotein comprising a large extracellular region, a single spanning transmembrane domain, an intracellular juxtamembrane region, a tyrosine kinase domain, and a C-terminal regulatory region. The extracellular region comprises four domains: Domains I and III are homologous ligand binding domains, and domains II and IV are cysteine rich domains (Ferguson, *Annu Rev Biophys.* (2008) 37:353-3).

The structured Domain III of human EGFR is targeted by the FDA licensed monoclonal antibody cetuximab (Erbitux®). Separating the cetuximab-binding ability of EGFR from its biological activity by selective truncation of the receptor offers the potential for an inert, fully human cell surface marker (Li et al., *Cancer Cell* (2005) 7(4):301-11; Wang et al., *Blood* (2011) 118(5):1255-63). However, a critical feature of a clinically useful cell surface marker is that the marker needs to be expressed at consistently high levels in the engineered cells such that the engineered cells can be sufficiently identified and targeted when needed.

SUMMARY OF THE INVENTION

The present disclosure provides a recombinant polypeptide comprising an extracellular region, a transmembrane region, and an intracellular region, wherein the extracellular region comprises a human epidermal growth factor receptor (EGFR) Domain III sequence, and the intracellular region (i) comprises a juxtamembrane domain that is net-neutral or net-positively charged in the first at least three amino acids (ii) but lacks an active EGFR tyrosine kinase domain. In some embodiments, the polypeptide does not have any active tyrosine kinase domain.

In some embodiments, more than half of the amino acids of the juxtamembrane domain are glycine, serine, arginine, lysine, threonine, asparagine, glutamine, aspartic acid, glutamic acid, tyrosine, tryptophan, histidine, and/or proline. In some embodiments, the amino acid at each position of the juxtamembrane domain is selected according to Table 1. For example, the juxtamembrane domain comprises RRRHIVRKR (SEQ ID NO:16), RRRHIVRK (SEQ ID NO:17), RRRHIVR (SEQ ID NO:18), RRRHIV (SEQ ID NO:19), RRRHI (SEQ ID NO:20), RRRH (SEQ ID NO:21), RRR, RKR, or RR. In certain embodiments, the intracellular region does not contain any residue that is phosphorylated.

In some embodiments, the human EGFR Domain III sequence may comprise SEQ ID NO:2 or a functional variant thereof such as a sequence comprising at least 90% identity to SEQ ID NO:2. In some embodiments, the extracellular region further comprises, C-terminal to the Domain III sequence, (i) a sequence derived from EGFR Domain IV, (ii) an artificial sequence, or (iii) both (i) and (ii). In particular embodiments, the extracellular region comprises amino acids 334-504, 334-525, or 334-645 of SEQ ID NO:1.

In some embodiments, the transmembrane region is derived from a human EGFR transmembrane domain, optionally comprising SEQ ID NO:5.

In some embodiments, the recombinant polypeptide comprises a signal peptide derived from human EGFR, human granulocyte-macrophage colony-stimulating factor (GM-CSF), human Ig kappa, mouse Ig kappa, or human CD33. For example, the signal peptide may comprise SEQ ID NO:22, 23, 24, or 25.

In particular embodiments, the recombinant polypeptide comprises SEQ ID NO:26, 27, 28, 29, 30, 31, 32, 33, 34, 35, 36, 37, 38, 39, or 40; or an amino acid sequence at least 90% identical thereto.

In another aspect, the present disclosure provides a nucleic acid molecule, such as an expression construct, comprising a coding sequence for a recombinant polypeptide of the present disclosure. In some embodiments, the nucleic acid molecule further comprises a coding sequence for a chimeric antigen receptor (CAR). The CAR may target, for example, a tumor antigen such as AFP, BCMA, CD19, CD20, CD22, CD123, EpCAM, GPC2, GPC3, HER2, MUC16, ROR1, or ROR2. In further embodiments, the CAR may be bispecific, targeting, e.g., CD19 and CD20 or CD19 and CD22. In certain embodiments, the coding sequences for the recombinant polypeptide and the CAR are operably linked to the same promoter (e.g., a constitutive or inducible promoter; for example, an MND promoter) such that the two coding sequences are co-transcribed, and optionally the two coding sequences are separated by (i) an internal ribosome entry site (IRES) or (ii) a coding sequence for a self-cleaving peptide (e.g., a 2A peptide) wherein the coding sequences for the recombinant polypeptide, the CAR, and the self-cleaving peptide are in frame with each other.

In some embodiments, the nucleic acid molecule further comprises a coding sequence for a third polypeptide, optionally wherein the third polypeptide is human c-Jun or a functional analog thereof. In further embodiments, the coding sequences for the recombinant polypeptide, the CAR, and the human c-Jun are operably linked to the same promoter (e.g., a constitutive or inducible promoter; for example, an MND promoter) such that the three coding sequences are co-transcribed, and optionally the three coding sequences are separated from each other by (i) an IRES or (ii) a coding sequence for a self-cleaving peptide (e.g., a 2A peptide) wherein the coding sequences for the recombinant polypeptide, the CAR, the human c-Jun, and the self-cleaving peptide(s) are in frame with each other.

In some embodiments, the nucleic acid molecule is a viral vector, optionally a lentiviral or retroviral vector.

In other aspects, the present disclosure provides a cell (e.g., autologous or allogeneic human T cells) comprising the nucleic acid molecule described herein; a recombinant virion comprising the nucleic acid molecule; and a pharmaceutical composition comprising the cell, the nucleic acid molecule, or the virion, and a pharmaceutically acceptable carrier.

In another aspect, the present disclosure provides a method of treating a patient in need thereof, comprising administering the cell to the patient, optionally wherein the cell is autologous or allogeneic. In some embodiments, the patient has cancer, and is given the T cell preparation described herein, where the T cells express a CAR, a T cell receptor (TCR), an engineered TCR, or a TCR mimic that is specific for a tumor antigen present in the cancer. In further embodiments, the method comprises administering to the patient an effective amount of an antibody specific for human EGFR once the patient has been treated (e.g., the cancer has regressed), wherein the antibody elicits cytotoxicity against T cells expressing the recombinant polypeptide, and optionally the antibody is $IgG_1$ or $IgG_2$ (e.g., cetuximab).

The present disclosure also provides the cell, the nucleic acid molecule, the recombinant virus, the pharmaceutical composition for use in the treatment methods, as well as the cell, the nucleic acid molecule, or the virus for the manufacture of a medicament for treating a patient as described herein.

In yet another aspect, the present disclosure provides a method of making a genetically engineered human cell (e.g., engineered T cells), comprising providing an isolated human cell, and introducing the nucleic acid molecule or recombinant virus described herein into the human cell.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE DRAWINGS

FIG. 1A: flow plot. FIG. 1B: a bar graph quantitating the geometric mean fluorescence intensity (gMFI) data from FIG. 1A. "DEARKAIAR": a juxtamembrane sequence DEARKAIARVKRESKRIVE-DAERLIREAAAASEKISREAERLI (SEQ ID NO:41). R12CAR: a CAR directed against ROR1. P2A: a self-cleaving peptide. EGFRt: a truncated human EGFR containing EGFR extracellular Domains III and IV and an EGFR transmembrane domain while lacking EGFR Domains I and II and EGFR intracellular sequence.

FIG. 2A depicts the domain structure of human EGFR from NCBI Reference Sequence NP_005219.2. The transmembrane domain is SEQ ID NO:5, and the juxtamembrane domain is SEQ ID NO:15 (full length sequence disclosed as SEQ ID NO:43). In the juxtamembrane domain, basic residues are indicated by red and "+," and acidic residues by blue and "-." Phosphorylated residues (green) are further described below.

FIG. 2B depicts the design of certain embodiments of the present EGFR-derived polypeptides (with transmembrane domain SEQ ID NO:5 without or with a juxtamembrane domain of RRR, SEQ ID NO:16, SEQ ID NO:12, or SEQ ID NO:13 (full length sequences disclosed as SEQ ID NOs:44-47, respectively, in order of appearance)). S. peptide: signal peptide. GMCSF: signal peptide derived from GM-CSF. Asterisks indicate the C-terminal end of the polypeptide.

FIGS. 3A-C show the expression of a series of bi-cistronic expression constructs for EGFR-derived polypeptides in primary T cells obtained from two donors and transduced with the expression constructs. FIG. 3A depicts the basic structure of the constructs, which include coding sequences for R12 CAR. FIGS. 3B and 3C show the gMFIs for bound ROR1-Fc fusion protein and AY13, respectively, in live R12 CAR+ transduced cells or live cells in the untransduced condition. Flow cytometry was performed eight days post transduction. FIGS. 3B and 3C disclose SEQ ID NOs:16, 12, 13, 16, 12, and 13, respectively, in order of appearance.

FIG. 4A discloses SEQ ID NOs:16, 12, 13, 16, 12, and 13, respectively, in order of appearance.

FIG. 4B discloses SEQ ID NOs:16, 12, and 13, respectively, in order of appearance.

FIGS. 5A and 5B disclose SEQ ID NOs:16, 12, and 13, respectively, in order of appearance.

FIG. 6A depicts the basic structure of the constructs. FIGS. 6B and 6C show the gMFIs for bound ROR1-Fc fusion protein and AY13, respectively, in live R12 CAR+ transduced cells or total live untransduced cells. Flow cytometry was performed eight days post transduction. FIGS. 6B and 6C each disclose SEQ ID NO:16.

FIG. 8 discloses SEQ ID NO:16.

FIG. 9 discloses SEQ ID NO:16.

FIG. 13B shows rebound kinetics of circulating B cells in the study shown in FIG. 13A. Two different doses of cetuximab were used as indicated.

FIG. 13C shows the frequency of B-cell-aplastic animals (below 3% CD19+ out of total CD45) following high (1 mg) or low (0.1 mg) dose cetuximab administration.

DETAILED DESCRIPTION OF THE INVENTION

Figure 1A:
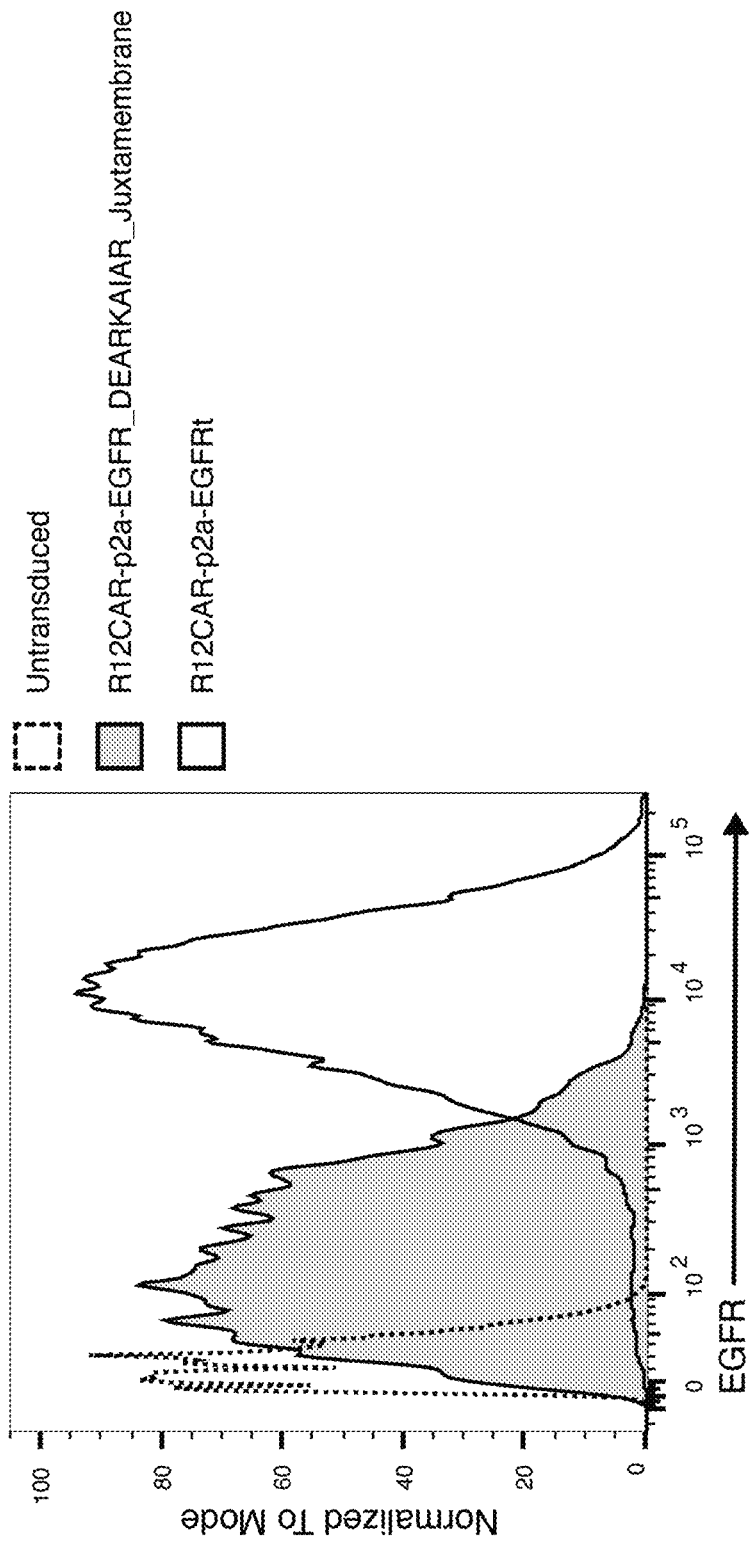
FIGS. 1A and 1B show the binding of anti-EGFR antibody AY13 to live CAR+ T cells transduced with R12CAR-P2A-EGFRt or R12CAR-P2A-EGFRt-DEARKAIAR, or to total live untransduced cells.

An important component of cell therapy is a compact, functionally inert cell surface marker that can be used for detecting, selecting, and enriching engineered cells, and for in vivo cell ablation. The present disclosure provides novel EGFR-derived proteins that can be used for these purposes. These proteins lack the ligand-binding and/or signal transduction functions of wildtype EGFR, but can still be recognized by common anti-EGFR antibodies.

Due to the design of their sequences, the present EGFR-derived proteins can be expressed at high levels on cell surface and therefore are particularly useful as a safety switch (suicide gene) in cell therapy. When the engineered cells in the therapy are no longer needed in the body, a pharmaceutical grade anti-EGFR antibody such as cetuximab, panitumumab, nimotuzumab, or necitumumab can be administered to the patient, thereby removing the engineered cells through antibody-dependent cellular cytotoxicity (ADCC), complement-dependent cytotoxicity (CDC), and/or antibody-dependent cellular phagocytosis (ADCP).

Unless otherwise indicated, EGFR as used herein refers to human EGFR. A human EGFR polypeptide sequence may be found at the UniProt database (Identifier No. P00533-1) and may have the following sequence:

```
   1 MRPSGTAGAA LLALLAALCP ASRALEEKKV CQGTSNKLTQ LGTFEDHFLS LQRMENNCEV
  61 VLGNLEITYV QRNYDLSFLK TIQEVAGYVL IALNTVERIP LENLQIIRGN MYYENSYALA
 121 VLSNYDANKT GLKELPMRNL QEILHGAVRF SNNPALCNVE SIQWRDIVSS DELSNMSMDF
 181 QNHLGSCQKC DPSCPNGSCW GAGEENCQKL TKIICAQQCS GRCRGKSPSD CCHNQCAAGC
 241 TGPRESDCLV CRKFRDEATC KDTCPPLMLY NPTTYQMDVN PEGKYSFGAT CVKKCPRNYV
 301 VTDHGSCVRA CGADSYEMEE DGVRKCKKCE GPCRKVCNGI GIGEFKDSLS INATNIKHFK
 361 NCTSISGDLH ILPVAFRGDS FTHTPPLDPQ ELDILKTVKE ITGFLLIQAW PENRTDLHAF
 421 ENLEIIRGRT KQHGQFSLAV VSLNITSLGL RSLKEISDGD VIISGNKNLC YANTINWKKL
 481 FGTSGQKTKI ISNRGENSCK ATGQVCHALC SPEGCWGPEP RDCVSCRNVS RGRECVDKCN
 541 LLEGEPREFV ENSECIQCHP ECLPQAMNIT CTGRGPDNCI QCAHYIDGPH CVKTCPAGVM
 601 GENNTLVWKY ADAGHVCHLC HPNCTYGCTG PGLEGCPTNG PKIPSIATGM VGALLLLLVV
 661 ALGIGLFMRR RHIVRKRTLR RLLQERELVE PLTPSGEAPN QALLRILKET EFKKIKVLGS
 721 GAFGTVYKGL WIPEGEKVKI PVAIKELREA TSPKANKEIL DEAYVMASVD NPHVCRLLGI
 781 CLTSTVQLIT QLMPFGCLLD YVREHKDNIG SQYLLNWCVQ IAKGMNYLED RRLVHRDLAA
 841 RNVLVKTPQH VKITDFGLAK LLGAEEKEYH AEGGKVPIKW MALESILHRI YTHQSDVWSY
 901 GVTVWELMTF GSKPYDGIPA SEISSILEKG ERLPQPPICT IDVYMIMVKC WMIDADSRPK
 961 FRELIIEFSK MARDPQRYLV IQGDERMHLP SPTDSNFYRA LMDEEDMDDV VDADEYLIPQ
1021 QGFFSSPSTS RTPLLSSLSA TSNNSTVACI DRNGLQSCPI KEDSFLQRYS SDPTGALTED
1081 SIDDTFLPVP EYINQSVPKR PAGSVQNPVY HNQPLNPAPS RDPHYQDPHS TAVGNPEYLN
1141 TVQPTCVNST FDSPAHWAQK GSHQISLDNP DYQQDFFPKE AKPNGIFKGS TAENAEYLRV
1201 APQSSEFIGA (SEQ ID NO: 1)
```

In the above sequence, the various EGFR domains are delineated as follows. The signal peptide spans amino acids 1-24. The extracellular sequence spans amino acids 25-645, wherein Domain I, Domain II, Domain III, and Domain IV span amino acids 25-188, 189-333, 334-504, and 505-645, respectively. The transmembrane domain spans amino acids 646-668. The intracellular domain spans amino acids 669-1,210, where the juxtamembrane domain spans amino acids 669-703 and the tyrosine kinase domain spans amino acids 704-1,210. Unless otherwise indicated, an EGFR amino acid position recited herein refers to the position in SEQ ID NO:1 or a corresponding position in a variant of SEQ ID NO:1 (e.g., a naturally occurring polymorphic variant or a genetically engineered variant).

I. EGFR-Derived Polypeptides

The recombinant polypeptides of the present disclosure are derived from EGFR but contain only a partial, rather than entire, sequence of EGFR. These polypeptides are cell surface proteins when expressed in mammalian cells. The polypeptides' extracellular, transmembrane, and intracellular regions are described below.

A. Extracellular Region

The extracellular region of the present EGFR-derived polypeptides comprises the epitope bound by an anti-EGFR antibody such as cetuximab. By way of example, the region may comprise Domain III of EGFR, such as the following Domain III sequence, or a functional variant thereof:

(SEQ ID NO: 2)
RKVCNGIGIG EFKDSLSINA TNIKHEKNCT SISGDLHILP VAFRGDSFTH TPPLDPQELD
ILKTVKEITG FLLIQAWPEN RTDLHAFENL EIIRGRTKQH GQFSLAVVSL NITSLGLRSL
KEISDGDVII SGNKNLCYAN TINWKKLEGT SGQKTKIISN RGENSCKATG Q

By "functional variant" is meant a sequence having sequence variations, such as deletions, insertions, and/or substitutions (e.g., conservative substitutions), that do not affect the sequence's desired biological function. A functional variant of SEQ ID NO:2 can be still bound by cetuximab.

To maintain the tertiary structure of the Domain III sequence, the extracellular region may further comprise additional EGFR sequences such as those that help stabilize disulfide bonds in the Domain III structure. For example, the extracellular region may comprise a Domain III sequence followed by a sequence derived from Domain IV of EGFR. A Domain IV-derived sequence may comprise the following Domain IV sequence:

(SEQ ID NO: 3)
VCHALCSPEG C$\boxed{\text{W}}$GPEPRDCV SCRNVSRGRE CVDKCNLLEG EPREFVENSE CIQCHPECLP
QAMNITCTGR GPDNCIQCAH YIDGPHCVKT CPAGVMGENN TLVWKYADAG HVCHLCHPNC
TYGCTGPGLE GCPTNGPKIP S A Domain IV-derived sequence may alternatively comprise a functional variant of SEQ ID NO:3. Such a functional variant can help maintain Domain III's tertiary structure to allow the binding of the polypeptide by an anti-EGFR antibody such as cetuximab. The functional variant may contain just a portion of a natural EGFR Domain IV, with or without additional sequences heterologous to EGFR (i.e., sequences that are not part of a natural EGFR sequence).

In some embodiments, a Domain IV-derived sequence includes a portion of a natural EGFR domain IV sequence, which portion includes amino acid residues involved in maintaining the structural fold of Domain III. Such amino acid residues include the W492 residue of mature EGFR (corresponding to W516 of SEQ ID NO:1 and W12 of SEQ ID NO:3; boxed in the sequences above) and optionally one or more residues adjacent to it. Structural analysis shows that W492 is important to the folding of EGFR Domain III, as this residue points into the core of Domain III and makes important side chain packing interactions. Examples of Domain IV-derived sequences are those including residues 492-496 of mature EGFR (corresponding to residues 516-520 of SEQ ID NO:1 and residues 12-16 of SEQ ID NO:3).

One particular example of a Domain IV-derived sequence is V$\boxed{\text{TGSG}}$WGPEPGGGS (SEQ ID NO:4), in which natural Domain IV's residues 482-491 and 497-621 are removed, V481 is connected to W492 through a synthetic four-residue linker (boxed above), and P496 is followed by a G/S linker (underlined above) linking it to the transmembrane region of the present polypeptide.

In some embodiments, the extracellular region of the present EGFR-derived polypeptides lacks the EGFR extracellular portion that binds ligands such as EGF and TGF-alpha. For example, the extracellular region does not include any sequence of Domain I and/or Domain II of EGFR or includes only partial sequences from either or both Domains.

In some embodiments, the extracellular region of the present polypeptides includes additional sequences. For example, the extracellular region may comprise a stalk region immediately N-terminal to the transmembrane domain. The stalk region may be, for example, a flexible stalk such as a G/S rich peptide linker or a structured stalk such as the CH2-CH3 domains from an antibody constant region or an extracellular domain from another protein. The extracellular region also may comprise an additional functional domain, such as antigen-binding domains (e.g., an scFv or a designed ankyrin repeat protein (DARPin)).

B. Transmembrane Region

The transmembrane region of the present polypeptides contains a hydrophobic sequence. This region may comprise an artificial sequence or may be derived from any transmembrane protein, which may be, for example, ERBB1 (EGFR), ERBB2 (HER2), ERBB3 (HER3), ERBB4 (HER4), INSR, IGF1R, INSRR, PGFRA, PGFRB, KIT, CSF1R, FLT3, VGFR1, VGFR2, VGFR3, FGFR1, FGFR2, FGFR3, FGFR4, PTK7, NTRK1, NTRK2, NTRK3, ROR1, ROR2, MUSK, MET, RON, UFO, TYRO3, MERTK, TIE1, TIE2, EPHA1, EPHA2, EPHA3, EPHA4, EPHA5, EPHA6, EPHA7, EPHA8, EPHAA, EPHB1, EPHB2, EPHB3, EPHB4, EPHB6, RET, RYK, DDR1, DDR2, ROS1, LMTK1, LMTK2, LMTK3, LTK, ALK, or STYK1.

One particular example of the transmembrane region is derived from EGFR, with the sequence of IATGMVGALLLLLVVALGIGLFM (SEQ ID NO:5), or a functional variant thereof.

C. Intracellular Region

The inventors have unexpectedly discovered that inclusion of an appropriate juxtamembrane domain in the intracellular region of the EGFR-derived protein markedly increases the protein's cell surface expression level. A juxtamembrane domain refers to an intracellular portion of a cell surface protein immediately C-terminal to the transmembrane domain. A high cell surface expression level ensures that the cell expressing the protein is recognized by an anti-EGFR antibody and thus ensures the eradication of the cell through, e.g., ADCC, CDC, and/or ADCP.

The juxtamembrane domain in the present polypeptide may be from 1 to 20 (e.g., 2-20, 3-20, 4-20, 5-20, 2-18, 3-18, 4-18, or 5-18) amino acids long. They also can be longer than 20 amino acids. In some embodiments, the first 1 or more (e.g., first 2, 3, 4, 5, 6, 7, 8, 9, 10, 11, 12, 13, 14, 15, 16, 17, 18, 19, or 20) amino acids of the intracellular region of the present polypeptide is a net-neutral or net-positively charged sequence (e.g., the number of arginine and lysine residues is greater than or equal to the number of aspartic acid and glutamic acid residues). In further embodiments, those first amino acids contain more than 30% (e.g., more than 40, 50, 60, 70, 80, or 90%) hydrophilic amino acids. Non-limiting examples of amino acid choices at each position of the sequence appended to the C-terminus of the transmembrane domain are shown in Table 1 below.

TABLE 1

| Position | Possible amino acids |
|---|---|
| 1 | R, K, C, L, H, S, N, A, Y, F, M, W, G, T, Q |
| 2 | R, K, C, G, L, Q, I, Y, F, M, N, S, T, W, H |
| 3 | R, K, L, C, M, W, Y, I, N, V, T, Q, A, F, G, S, D, E, H |
| 4 | R, K, H, Q, G, S, C, N, V, W, P, F, T, D, E, Y |
| 5 | R, K, Q, C, G, A, I, L, N, P, T, W, S, D, E, Y, H |
| 6 | K, R, Q, P, V, D, N, Y, I, E, C, A, H, W, G, F, S, T |
| 7 | K, R, or another amino acid |
| 8 | K, R, S, Q, G, L, I, T, P, Y, N, A, F, W, D, H, E |
| 9 | K, R, G, L, Y, E, F, Q, S, A, H, P, T, N, D, W |
| 10 | G, A, E, R, D, K, T, Y, V, F, S, M, Q, L, N, P, W, H |
| 11 | K, R, Q, S, A, E, L, T, P, N, I, D, F, G, V, Y, W, H |
| 12 | Any amino acid |
| 13 | S, E, R, F, K, P, L, Y, D, or another amino acid |
| 14 | T, R, S, E, A, P, Q, K, N, V, or another amino acid |
| 15 | D, E, S, L, P, A, R, V, M, or another amino acid |
| 16 | E, V, Q, A, or another amino acid |
| 17 | E, L, D, Q, V, A, K, or another amino acid |
| 18 | Any amino acid |
| 19 | Any amino acid |
| 20 | E, G, L, R, S, V, Y, K, D, or another amino acid |

Some non-limiting examples of such juxtamembrane domains are shown below:

TABLE 2

| SEQ ID NO | Sequence | Net charge |
|---|---|---|
| n/a | K | +1 |
| n/a | KR | +2 |
| n/a | KRK | +3 |
| n/a | KSR | +2 |
| 6 | KSGSGS | +1 |
| n/a | SKR | +2 |
| 7 | KRSD | +1 |
| 8 | KRSDK | +2 |
| 9 | SGGGG | 0 |
| 10 | SGAGG | 0 |
| 11 | KRADK | +2 |
| 12 | RRRSGGGGSGGGGS | +3 |

TABLE 2-continued

| SEQ ID NO | Sequence | Net charge |
|---|---|---|
| 13 | SGGGGSGGGGS | 0 |
| 14 | (GGGGS)n, n > 1 | 0 |

The present juxtamembrane domain may be derived from the juxtamembrane region of a natural cell surface protein, such as a juxtamembrane region (e.g., the entire or partial sequence of the first 20 juxtamembrane amino acids) of a human receptor tyrosine kinase that interacts with phosphatidylcholine (PC), phosphatidylserine (PS), or phosphatidylinositol-4,5-bisphosphate (PIP2) (see, e.g., Hedger et al., *Sci Rep.* (2015) 5: 9198). Examples of receptor tyrosine kinases are ERBB1 (EGFR), ERBB2 (HER2), ERBB3 (HER3), ERBB4 (HER4), INSR, IGF1R, INSRR, PGFRA, PGFRB, KIT, CSF1R, FLT3, VGFR1, VGFR2, VGFR3, FGFR1, FGFR2, FGFR3, FGFR4, PTK7, NTRK1, NTRK2, NTRK3, ROR1, ROR2, MUSK, MET, RON, UFO, TYRO3, MERTK, TIE1, TIE2, EPHA1, EPHA2, EPHA3, EPHA4, EPHA5, EPHA6, EPHA7, EPHA8, EPHAA, EPHB1, EPHB2, EPHB3, EPHB4, EPHB6, RET, RYK, DDR1, DDR2, ROS1, LMTK1, LMTK2, LMTK3, LTK, ALK, and STYK1. If desired, the derived sequence may contain mutations (e.g., substitutions or deletions) that remove residues known to be phosphorylated so as to circumvent any unintended signal transducing ability of the present protein.

In some embodiments, the juxtamembrane domain of the present polypeptide comprises a juxtamembrane region of EGFR, such as:

RRRHIVRKR☒LRRLLQERELVEPL☒P
☒GEAPNQAL (SEQ ID NO:15).

In some embodiments, an EGFR-derived juxtamembrane domain is derived from the first 19 amino acids of a natural EGFR juxtamembrane region (e.g., SEQ NO ID:15) and does not include the entirety of the remaining portion of the natural juxtamembrane region, so as to avoid dimerization of the present polypeptide. In some embodiments, the residues known to be phosphorylated (boxed above, corresponding to T678, T693, and S695 of SEQ ID NO:1) are deleted or substituted. Nonlimiting examples of EGFR-derived juxtamembrane domains comprise one of the following sequences:

TABLE 3

| SEQ ID NO | Sequence | Net charge |
|---|---|---|
| 16 | RRRHIVRKR | +6 |
| 17 | RRRHIVRK | +5 |
| 18 | RRRHIVR | +4 |
| 19 | RRRHIV | +3 |
| 20 | RRRHI | +3 |
| 21 | RRRH | +3 |
| n/a | RRR | +3 |
| n/a | RKR | +3 |
| n/a | RR | +2 |
| n/a | R | +1 |

In some embodiments, the intracellular region also includes an additional sequence C-terminal to the juxtamembrane domain, e.g., a functional domain (e.g., a switch receptor).

The present EGFR-derived protein lacks a functional tyrosine kinase domain of EGFR such that the protein lacks signal transducing ability. For example, the protein lacks the entirety of a region that corresponds to amino acids 704-1, 210 of SEQ ID NO:1. In some embodiments, the intracellular region does not contain any potential phosphorylation motif.

D. Signal Peptide

In some embodiments, the coding sequence for the present polypeptide includes a coding sequence for a signal peptide. The signal peptide may facilitate the cell surface expression of the polypeptide and is cleaved from the mature polypeptide. The signal peptide may be derived from that of any cell surface protein or secreted protein. For example, the signal peptide may be a signal peptide shown below:

TABLE 4

| SEQ ID NO | Source | Sequence |
|---|---|---|
| 22 | EGFR | MRPSGTAGAALLALLAALCPASRA |
| 23 | GM-CSF | MLLLVTSLLLCELPHPAFLLIP |

TABLE 4-continued

| SEQ ID NO | Source | Sequence |
|---|---|---|
| 24 | human Ig kappa | MVLQTQVFISLLLWISGAYG |
| 25 | human CD33 | MPLLLLLPLLWAGALA |

The various domains described above for the extracellular, transmembrane, and intracellular regions of the present polypeptides may be linked directly or through a peptide linker.

E. Examples of EGFR-Derived Polypeptides

In some embodiments, the present polypeptide comprises, consists of, or consists essentially of EGFR Domain III (italicized), Domain IV (underlined), and transmembrane domain, with a juxtamembrane domain (not shown) appended to the C-terminus of the transmembrane domain, with or without a signal peptide (not shown):

(SEQ ID NO: 26)
*RKVCNGIGIGEFKDSLSINATNIKHFKNCTSISGDLHILPVAFRGDSFTHTPPLDPQELDILKTV*

*KEITGELLIQAWPENRTDLHAFENLEIIRGRTKQHGQFSLAVVSLNITSLGLRSLKEISDGDVII*

*SGNKNLCYANTINWKKLFGTSGQKTKIISNRGENSCKATGQ*VCHALCSPEGCWGPEPRDCVSCRN

VSRGRECVDKCNLLEGEPREFVENSECIQCHPECLPQAMNITCTGRGPDNCIQCAHYIDGPHCVK

TCPAGVMGENNTLVWKYADAGHVCHLCHPNCTYGCTGPGLEGCPTNGPKIPSIATGMVGALLLLL

VVALGIGLFM

In some embodiments, the present polypeptide comprises, consists of, or consists essentially of EGFR Domain III (italicized), modified portion of EGFR Domain IV (boldfaced and underlined), EGFR transmembrane domain, and a juxtamembrane domain (not shown) appended to the C-terminus of the transmembrane domain, with or without a signal peptide (not shown):

(SEQ ID NO: 27)
*RKVCNGIGIGEFKDSLSINATNIKHEKNCTSISGDLHILPVAFRGDSFTHTPPLDPQELDILKTV*

*KEITGELLIQAWPENRTDLHAFENLEIIRGRTKQHGQFSLAVVSLNITSLGLRSLKEISDGDVII*

*SGNKNLCYANTINWKKLFGTSGQKTKIISNRGENSCKATGQ'__VCHALCSPEGCWGPEPRDCVSGGP__

__S__IATGMVGALLLLLVVALGIGLFM

In some embodiments, the present polypeptide comprises, consists of, or consists essentially of EGFR Domain III (italicized), synthetic sequence (boldfaced and underlined), EGFR transmembrane domain, and a juxtamembrane domain (not shown) appended to the C-terminus of the transmembrane domain, with or without a signal peptide (not shown):

(SEQ ID NO: 28)
*RKVCNGIGIGEFKDSLSINATNIKHFKNCTSISGDLHILPVAFRGDSFTHTPPLDPQELDILKTV*

*KEITGFLLIQAWPENRTDLHAFENLEIIRGRTKQHGQFSLAVVSLNITSLGLRSLKEISDGDVII*

*SGNKNLCYANTINWKKLFGTSGQKTKIISNRGENSCKATGQ*__TGSGWGPEPGGGSPS__IATGMVGAL

LLLLVVALGIGLFM

In some embodiments, the present polypeptide comprises, consists of, or consists essentially of a GM-CSF signal peptide (boldfaced), EGFR Domain III(italicized), EGFR domain IV (underlined), EGFR transmembrane domain (boldfaced and italicized) and a juxtamembrane domain having the sequence of RRR:

(SEQ ID NO: 29)
MLLLVTSLLLCELPHPAFLLI_RKVCNGIGIGEFKDSLSINATNIKHFKNCTSISGDLHILPVAF_

_RGDSFTHTPPLDPQELDILKTVKEITGELLIQAWPENRTDLHAFENLEIIRGRTKQHGQFSLAVV_

_SLNITSLGLRSLKEISDGDVIISGNKNLCYANTINWKKLFGTSGQKTKIISNRGENSCKATGQV_C

HALCSPEGCWGPEPRDCVSCRNVSRGRECVDKCNLLEGEPREFVENSECIQCHPECLPQAMNITC

TGRGPDNCIQCAHYIDGPHCVKTCPAGVMGENNTLVWKYADAGHVCHLCHPNCTYGCTGPGLEGC

PTNGPKIPS_IATGMVGALLLLLVVALGIGLFM_RRR

In some embodiments, the present polypeptide comprises, consists of, or consists essentially of a GM-CSF signal peptide (boldfaced), EGFR Domain III(italicized), EGFR Domain IV (underlined), EGFR transmembrane domain (boldfaced and italicized), and a juxtamembrane domain having the sequence of RRRHIVRKR (SEQ ID NO:16):

(SEQ ID NO: 30)
MLLLVTSLLLCELPHPAFLLI_RKVCNGIGIGEFKDSLSINATNIKHFKNCTSISGDLHILPVAF_

_RGDSFTHTPPLDPQELDILKTVKEITGELLIQAWPENRTDLHAFENLEIIRGRTKQHGQFSLAVV_

_SLNITSLGLRSLKEISDGDVIISGNKNLCYANTINWKKLFGTSGQKTKIISNRGENSCKATGQV_C

HALCSPEGCWGPEPRDCVSCRNVSRGRECVDKCNLLEGEPREFVENSECIQCHPECLPQAMNITC

TGRGPDNCIQCAHYIDGPHCVKTCPAGVMGENNTLVWKYADAGHVCHLCHPNCTYGCTGPGLEGC

PTNGPKIPS_IATGMVGALLLLLVVALGIGLFM_RRRHIVRKR

In some embodiments, the present polypeptide comprises, consists of, or consists essentially of a GM-CSF signal peptide (boldfaced), EGFR Domain III(italicized), EGFR Domain IV (underlined), EGFR transmembrane domain (boldfaced and italicized), and a juxtamembrane domain having the sequence of RRRSGGGGSGGGGS (SEQ ID NO:12):

(SEQ ID NO: 31)
MLLLVTSLLLCELPHPAFLLI_RKVCNGIGIGEFKDSLSINATNIKHFKNCTSISGDLHILPVAF_

_RGDSFTHTPPLDPQELDILKTVKEITGELLIQAWPENRTDLHAFENLEIIRGRTKQHGQFSLAVV_

_SLNITSLGLRSLKEISDGDVIISGNKNLCYANTINWKKLFGTSGQKTKIISNRGENSCKATGQV_C

HALCSPEGCWGPEPRDCVSCRNVSRGRECVDKCNLLEGEPREFVENSECIQCHPECLPQAMNITC

TGRGPDNCIQCAHYIDGPHCVKTCPAGVMGENNTLVWKYADAGHVCHLCHPNCTYGCTGPGLEGC

PTNGPKIPS_IATGMVGALLLLLVVALGIGLFM_RRRSGGGGSGGGGS

In some embodiments, the present polypeptide comprises, consists of, or consists essentially of a GM-CSF signal peptide (boldfaced), EGFR Domain III(italicized), EGFR Domain IV (underlined), EGFR transmembrane domain (boldfaced and italicized), and a juxtamembrane domain having the sequence of SGGGGSGGGGS (SEQ ID NO:13)

(SEQ ID NO: 32)
MLLLVTSLLLCELPHPAFLLIP*RKVCNGIGIGEFKDSLSINATNIKHEKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATGQV*C

HALCSPEGCWGPEPRDCVSCRNVSRGRECVDKCNLLEGEPREFVENSECIQCHPECLPQAMNITC

TGRGPDNCIQCAHYIDGPHCVKTCPAGVMGENNTLVWKYADAGHVCHLCHPNCTYGCTGPGLEGC

PTNGPKIPS*IATGMVGALLLLLVVALGIGLFM*SGGGGSGGGGS

In some embodiments, the present polypeptide comprises, consists of, or consists essentially of a GM-CSF signal peptide (boldfaced), EGFR Domain III(italicized), modified portion of EGFR Domain IV (underlined), EGFR transmembrane domain (boldfaced and italicized), and a juxtamembrane domain having the sequence of RRR:

(SEQ ID NO: 33)
MLLLVTSLLLCELPHPAFLLIP*RKVCNGIGIGEFKDSLSINATNIKHEFKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATGQV*C

HALCSPEGCWGPEPRDCVSGGPS*IATGMVGALLLLLVVALGIGLFM*RRR

In some embodiments, the present polypeptide comprises, consists of, or consists essentially of a GM-CSF signal peptide (boldfaced), EGFR Domain III(italicized), modified portion of EGFR Domain IV (underlined), EGFR transmembrane domain (boldfaced and italicized), and a juxtamembrane domain having the sequence of RRRHIVRKR (SEQ ID NO:16):

(SEQ ID NO: 34)
MLLLVTSLLLCELPHPAFLLIP*RKVCNGIGIGEFKDSLSINATNIKHFKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATGQV*C

HALCSPEGCWGPEPRDCVSGGPS*IATGMVGALLLLLVVALGIGLFM*RRRHIVRKR

In some embodiments, the present polypeptide comprises, consists of, or consists essentially of a GM-CSF signal peptide (boldfaced), EGFR Domain III(italicized), modified portion of EGFR Domain IV (underlined), EGFR transmembrane domain (boldfaced and italicized), and a juxtamembrane domain having the sequence of RRRSGGGGSGGGGS (SEQ ID NO:12):

(SEQ ID NO: 35)
MLLLVTSLLLCELPHPAFLLIP*RKVCNGIGIGEFKDSLSINATNIKHFKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATGQV*C

HALCSPEGCWGPEPRDCVSGGPS*IATGMVGALLLLLVVALGIGLFM*RRRSGGGGSGGGGS

In some embodiments, the present polypeptide comprises, consists of, or consists essentially of a GM-CSF signal peptide (boldfaced), EGFR Domain III(italicized), modified portion of EGFR Domain IV (underlined), EGFR transmembrane domain (boldfaced and italicized), and a juxtamembrane domain having the sequence of SGGGGSGGGGS (SEQ ID NO:13):

(SEQ ID NO: 36)
MLLLVTSLLLCELPHPAFLLIP*RKVCNGIGIGEFKDSLSINATNIKHFKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATG*QVC

HALCSPEGCWGPEPRDCVSGGPS*IATGMVGALLLLLVVALGIGLFM*SGGGGSGGGGS

In some embodiments, the present polypeptide comprises, consists of, or consists essentially of a GM-CSF signal peptide (boldfaced), EGFR Domain III(italicized), synthetic sequence (underlined), EGFR transmembrane domain (boldfaced and italicized), and a juxtamembrane domain having the sequence of RRR:

(SEQ ID NO: 37)
MLLLVTSLLLCELPHPAFLLIP*RKVCNGIGIGEFKDSLSINATNIKHFKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATG*QTG

SGWGPEPGGGSPS*IATGMVGALLLLLVVALGIGLFM*RRR

In some embodiments, the present polypeptide comprises, consists of, or consists essentially of a GM-CSF signal peptide (boldfaced), EGFR Domain III(italicized), synthetic sequence (underlined), EGFR transmembrane domain (boldfaced and italicized), and a juxtamembrane domain having the sequence of RRRHIVRKR (SEQ ID NO:16):

(SEQ ID NO: 38)
MLLLVTSLLLCELPHPAFLLIP*RKVCNGIGIGEFKDSLSINATNIKHFKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATG*QTG

SGWGPEPGGGSPS*IATGMVGALLLLLVVALGIGLFM*RRRHIVRKR

In some embodiments, the present polypeptide comprises, consists of, or consists essentially of a GM-CSF signal peptide (boldfaced), EGFR Domain III(italicized), synthetic sequence (underlined), EGFR transmembrane domain (boldfaced and italicized), and a juxtamembrane domain having the sequence of RRRSGGGGSGGGGS (SEQ ID NO:12):

(SEQ ID NO: 39)
MLLLVTSLLLCELPHPAFLLIP*RKVCNGIGIGEFKDSLSINATNIKHEKNCTSISGDLHILPVAF*

*RGDSFTHTPPLDPQELDILKTVKEITGELLIQAWPENRTDLHAFENLEIIRGRTKQHGQFSLAVV*

*SLNITSLGLRSLKEISDGDVIISGNKNLCYANTINWKKLFGTSGQKTKIISNRGENSCKATG*QTG

SGWGPEPGGGSPS*IATGMVGALLLLLVVALGIGLFM*RRRSGGGGSGGGGS

In some embodiments, the present polypeptide comprises, consists of, or consists essentially of a GM-CSF signal peptide (boldfaced), EGFR Domain III(italicized), synthetic sequence (underlined), EGFR transmembrane domain (boldfaced and italicized), and a juxtamembrane domain having the sequence of SGGGGSGGGGS (SEQ ID NO:13):

(SEQ ID NO: 40)
MLLLVTSLLLCELPHPAFLLIPRKVCNGIGIGEFKDSLSINATNIKHFKNCTSISGDLHILPVAF

RGDSFTHTPPLDPQELDILKTVKEITGELLIQAWPENRTDLHAFENLEIIRGRTKQHGQFSLAVV

SLNITSLGLRSLKEISDGDVIISGNKNLCYANTINWKKLFGTSGQKTKIISNRGENSCKATGQTG

SGWGPEPGGGSPS*IATGMVGALLLLLVVALGIGLFM*SGGGGSGGGGS

Also provided in the present disclosure are EGFR-derived polypeptides that are at least 90% (e.g., at least 91, 92, 93, 94, 95, 96, 97, 98, or 99%) identical in sequence to the above exemplified sequences.

II. Expression Constructs for the EGFR-Derived Proteins

The present disclosure provides expression constructs suitable for expressing the EGFR-derived proteins in cells that are used in cell therapy. An expression construct of the present disclosure includes an expression cassette comprising a coding sequence for the EGFR-derived polypeptide (preferably including a signal peptide) linked operably to one or more transcriptional regulatory elements. As used herein, "transcriptional regulatory elements" refer to nucleotide sequences in the expression construct that control expression of the coding sequence, for example, by regulating the tissue-specific expression patterns and transcription efficiency of the EGFR-derived polypeptide coding sequence, the stability of the RNA transcripts, and the translation efficiency of the RNA transcripts. These elements may be one or more of a promoter, a Kozak sequence, an enhancer, an RNA-stabilizing element (e.g., a WPRE sequence), a polyadenylation signal, and any combination thereof.

In some embodiments, the expression cassette contains a mammalian promoter that is constitutively active or inducible in the target cells. Examples of useful promoters are, without limitation, a Moloney murine leukemia virus (Mo-MuLV) LTR, an MND (a synthetic promoter containing the U3 region of a modified MoMuLV LTR with myeloproliferative sarcoma virus enhancer), a Rous sarcoma virus (RSV) LTR, a cytomegalovirus (CMV) promoter, a CMV immediate early promoter, a simian virus 40 (SV40) promoter, a dihydrofolate reductase (DHFR) promoter, a R-actin promoter, a phosphoglycerate kinase (PGK) promoter, an EF1α promoter, a thymidine kinase (TK) promoter, a tetracycline responsive promoter (TRE), an E2 factor (E2F) promoter, the human telomerase reverse transcriptase (hTERT) promoter, and an RU-486-responsive promoter.

In certain embodiments, the expression cassette also comprises additional regulatory sequences, for example, an internal ribosome entry site (IRES) or a sequence encoding a self-cleaving peptide to allow co-expression of another polypeptide in addition to the EGFR-derived polypeptide. Examples of self-cleaving peptides (also known as ribosomal skipping peptides) are 2A peptides, which are viral derived peptides with a typical length of 18-22 amino acids and include T2A, P2A, E2A, and F2A (Liu et al., *Sci Rep.* (2017) 7:2193).

In some embodiments, the present expression construct also expresses an antigen receptor and/or another additional polypeptide. The antigen receptor may be, for example, an antibody, an engineered antibody such as an scFv, a CAR, an engineered TCR, a TCR mimic (e.g., an antibody-T cell receptor (abTCR) or a chimeric antibody-T cell receptor (caTCR)), or a chimeric signaling receptor (CSR). By way of example, an abTCR may comprise an engineered TCR in which the antigen-binding domain of a TCR (e.g., an alpha/beta TCR or a gamma/delta TCR) has been replaced by that of an antibody (with or without the antibody's constant domains); the engineered TCR then becomes specific for the antibody's antigen while retaining the TCR's signaling functions. A CSR may comprise (1) an extracellular binding domain (e.g., natural/modified receptor extracellular domain, natural/modified ligand extracellular domain, scFv, nanobody, Fab, DARPin, and affibody), (2) a transmembrane domain, and (3) an intracellular signaling domain (e.g., a domain that activates transcription factors, or recruits and/or activates JAK/STAT, kinases, phosphatases, and ubiquitin; SH3; SH2; and PDZ). See, e.g., EP340793B1, WO 2017/070608, WO 2018/200582, WO 2018/200583, WO 2018/200585, and Xu et al., *Cell Discovery* (2018) 4:62.

The antigen receptor may target an antigen of interest (e.g., a tumor antigen or an antigen of a pathogen). The antigens may include, without limitation, AFP (alpha-fetoprotein), αvβ6 or another integrin, BCMA, B7-H3, B7-H6, CA9 (carbonic anhydrase 9), CCL-1 (C-C motif chemokine ligand 1), CD5, CD19, CD20, CD21, CD22, CD23, CD24, CD30, CD33, CD38, CD40, CD44, CD44v6, CD44v7/8, CD45, CD47, CD56, CD66e, CD70, CD74, CD79a, CD79b, CD98, CD123, CD138, CD171, CD352, CEA (carcinoembryonic antigen), Claudin 18.2, Claudin 6, c-MET, DLL3 (delta-like protein 3), DLL4, ENPP3 (ectonucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-α (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRC5D (G Protein Coupled Receptor 5D), HER2, HER3, HER4, hepatitis B surface antigen, HLA-A1 (human leukocyte antigen A1), HLA-A2 (human leukocyte antigen A2), HMW-MAA (human high molecular weight-melanoma-associated antigen), IGF1R (insulin-like growth factor 1 receptor), Ig kappa, Ig lambda, IL-22Ra (IL-22 receptor alpha), IL-13Ra2 (IL-13 receptor alpha 2), KDR (kinase insert domain receptor), LI cell adhesion molecule (LI-CAM), Liv-1, LRRC8A (leucine rich repeat containing 8 Family member A), Lewis Y, melanoma-associated antigen (MAGE)-A1, MAGE-A3, MAGE-A6, MART-1 (melan A), murine cytomegalovirus (MCMV), MCSP (melanoma-associated chondroitin sulfate proteoglycan), mesothelin, mucin 1 (MUC1), MUC16, MHC/peptide complexes (e.g., HLA-A complexed with peptides derived from AFP, KRAS, NY-ESO, MAGE-A, and WTi), NCAM (neural cell adhesion molecule), Nectin-4, NKG2D (natural killer group 2 member D) ligands, NY-ESO, oncofetal antigen, PD-1, PD-L1, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), STEAP1 (six transmembrane epithelial antigen of the prostate 1), survivin, TAG72 (tumor-associated glycoprotein 72), TPBG (trophoblast glycoprotein), Trop-2, VEGFR1 (vascular endothelial growth factor receptor 1), VEGFR2, and antigens from HIV, HBV, HCV, HPV, and other pathogens.

In some embodiments, the antigen receptor may be bispecific and target two different antigens, such as two of the antigens listed above. For example, the antigen receptor, such as a CAR, targets CD19 and CD20, or CD19 and CD22.

The additional polypeptide may be, for example, a cytokine (e.g., IL-2, IL-7, IL-12, IL-15, IL-23, and engineered variants thereof), a cytokine receptor (e.g., IL-12R, IL-7R, and engineered variants thereof), a chemokine, a transcription factor (e.g., c-Jun or c-fos; see, e.g., WO 2019/118902), functional analogs thereof, other engineered receptors (e.g. TGFBetaR), and other engineered effectors (e.g., secretory secondary effector; see, e.g., WO 2018/200585). By "functional analog" is meant a molecule that has the same or similar biological activity of interest as the cognate polypeptide or peptide even though there are sequence differences between it and the cognate molecule.

The coding sequences of these additional polypeptides may be under the control of different promoters from the EGFR-derived polypeptide coding sequence. Alternatively, they may be under the control of the same promoter as the EGFR-derived coding sequence but are separated from each other through an IRES or an in-frame coding sequence for a 2A peptide, such that the coding sequences can be co-expressed under the same promoter.

The expression constructs of the present disclosure may be delivered to target cells in vitro, ex vivo or in vivo by suitable means such as electroporation, sonoporation, viral transduction, lipofection, microinjection, biolistics, virosomes, liposomes, immunoliposomes, and nanoparticles (e.g., polymeric or lipid nanoparticles). In some embodiments, the expression constructs may be viral vectors and are delivered to the target cells through recombinant viruses containing the constructs. The viral vectors contain the EGFR-derived polypeptide expression cassette and minimal viral sequences required for packaging and subsequent integration into a host (if applicable). The missing viral functions are supplied in trans by the packaging cell line used to package the recombinant virus. The viral vector may be, for example, vaccinia vectors, adenoviral vectors, lentiviral vectors, poxyviral vectors, herpes simplex viral vectors, adeno-associated viral vectors, retroviral vectors, and hybrid viral vectors. In part depending on virus type, the EGFR-derived polypeptide expression cassette may be stably integrated into the genome of the target cells, or remain in the cells episomally. Integration into the host genome is possible with retrovirus and lentivirus.

III. Pharmaceutical Use of Cells Expressing the EGFR-Derived Proteins

The present expression constructs may be introduced into cells used in cell therapy. These cells are, for example, multipotent cells such as hematopoietic stem cells, various progenitor or precursor cells of hematopoietic lineages, and various immune cells (e.g., human autologous or allogeneic T, natural killer (NK), dendritic, or B cells). These cells may also be pluripotent stem cells (PSCs) such as human embryonic stem cells and induced PSCs, which can be used to generate therapeutic cell populations. In some embodiments, pluripotent and multipotent cells are differentiated into a desired cell type in vitro before being implanted into the patient.

In some embodiments, the present disclosure provides engineered T lymphocytes that express the EGFR-derived protein and from the same construct or from a separate construct, one or more additional polypeptides. The one or more additional polypeptides may be an antigen receptor such as an antibody, an engineered antibody such as an scFv, a CAR, an engineered TCR, a TCR mimic (e.g., an abTCR or caTCR), or a CSR, as described above. The antigen receptor may target, for example, the antigens described above. The additional polypeptide also may be, for example, a cytokine, a cytokine receptor, a chemokine, a transcription factor, a functional analog of the foregoing, another engineered receptor, or an engineered effector as described above. The coding sequences of these additional polypeptides may be under the control of different promoters from the EGFR-derived polypeptide coding sequence. In some embodiments, the present disclosure provides engineered autologous or allogeneic NK cells expressing engineered receptors, and engineered B lymphocytes expressing an antibody, an engineered antibody, or an engineered tissue-specific cell expressing a therapeutic protein.

The genetically engineered cells described herein may be provided in a pharmaceutical composition containing the cells and a pharmaceutically acceptable carrier. The pharmaceutically acceptable carrier may be cell culture medium that optionally does not contain any animal-derived component. For storage and transportation, the cells may be cryopreserved. Prior to use, the cells may be thawed, and diluted in a sterile cell medium. The cells may be administered into the patient systemically (e.g., through intravenous injection or infusion), or locally (e.g., through direct injection to a local tissue, e.g., at the site of a solid tumor).

A therapeutically effective number of engineered cells are administered to the patient. As used herein, the term "therapeutically effective" refers to a number of cells or amount of pharmaceutical composition that is sufficient, when administered to a human subject suffering from or susceptible to a disease, disorder, and/or condition, to treat, prevent, and/or delay the onset or progression of the symptom(s) of the disease, disorder, and/or condition. For example, a therapeutically effective amount of engineered CAR-T cells is an amount that is sufficient to cause tumor growth arrest, tumor regression, prevention of tumor metastasis, or prevention of tumor recurrence.

Once the engineered cells are no longer desired in a patient, e.g., when the cells do not function properly or when the therapeutic goal has been achieved, an anti-EGFR antibody may be administered to the patient at an amount that is sufficient to cause antibody-mediated killing of the cells. For example, cetuximab (e.g., Erbitux©) can be administered through infusion at one or more doses determined as appropriate for the number of engineered cells remaining in the patient.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to the manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

EXAMPLES

In order for the present disclosure to be better understood, the following examples are set forth. These examples are for illustration only and are not to be construed as limiting the scope of the present disclosure in any manner.

Example 1: Surface Expression of EGFR-Derived Polypeptides

This example describes studies analyzing the effects of various juxtamembrane domains on the cell surface expression levels of EGFR-derived polypeptides.

Methods

Expression Constructs

Lentiviral constructs were generated with bi-cistronic or tri-cistronic expression cassettes. In constructs with bi-cistronic expression cassettes, the coding sequences for (i) a ROR1-specific R12 CAR, (ii) a P2A self-cleaving peptide, and (iii) EGFRt (a truncated EGFR having only Domains III and IV and the transmembrane domain; SEQ ID NO:26) or a variant having additionally an intracellular juxtamembrane domain were linked in frame and placed under the control of an MND promoter. In constructs with tri-cistronic expression cassettes, the coding sequences for (i) c-Jun, (ii) a P2A peptide, (iii) a ROR1-specific R12 CAR, (iv) a P2A peptide; and (v) EGFRt or a variant having additionally an intracellular juxtamembrane domain were linked in frame and placed under the control of an MND promoter. The R12 CAR was derived from the R12 anti-ROR1 antibody (Yang et al., *PLoS One.* (2011) 6:e21018) and contains a CD28-derived transmembrane domain, a 4-1BB costimulatory domain, and a CD3 zeta signaling domain.

Cell Culture and Lentiviral Transduction

Jurkat cells were obtained from American Type Culture Collection (ATCC; Manassas VA). For lentiviral transduction, the cells were fed with fresh media 4-16 hours before transduction, followed by incubation with lentivirus in complete media+LentiBOOST™ at the manufacturer's recommended concentration (Sirion Biotech). Eighteen hours after transduction, lentivirus and LentiBOOST™ were diluted by addition of 1 volume of fresh media.

Pre-selected, cryopreserved primary human CD4+ and CD8+ T cells from normal donors were obtained from Bloodworks (Seattle WA). Human T cells were cultured in OpTmizer medium (Thermo Fisher) supplemented with Immune Cell Serum Replacement (Thermo Fisher), 2 mM L-glutamine (Gibco), 2 mM Glutamax (Gibco), 200 IU/ml IL-2 (R&D systems), 120 IU/ml IL-7 (R&D systems), and 20 IU/ml IL-15 (R&D systems). For lentiviral transduction, the T cells were stimulated with a 1:100 dilution of T cell TransAct (Miltenyi) for 30 hours. Virus was then added to the T cells for 18-24 hours. Stimulation and viral infection were then terminated by addition of 7 volumes of fresh media without TransAct, and cells were cultured for 3-7 additional days before analysis.

Flow Cytometry

Flow cytometry was performed on a Ze5 cytometer (Bio-Rad Laboratories). To determine expression of cell surface markers, about $1 \times 10^5$ to $2 \times 10^5$ total cells were transferred to a V bottom 96 well culture dish (Corning). Cells were washed twice with flow cytometry staining buffer (eBioscience), and then stained with the relevant reagents in a total volume of 50 μl flow cytometry staining buffer for 30 minutes on ice. After staining, the cells were washed twice with flow cytometry staining buffer, fixed in FluoroFix Buffer (BioLegend), and kept at 4° C. in the dark until analysis. Flow cytometry data was analyzed using FlowJo 10 (Tree Star).

For flow cytometry analysis, AY13 antibody labeled with fluorochrome BV421 (BioLegend) was used to detect EGFR variants. Purified recombinant ROR1 fused to human Ig Fc was produced in-house and conjugated to Alexa 647 dye for detecting R12 CAR. eFluor 780 Fixable Viability dye (eBioscience) was included during primary antibody stain at a 1:8000 dilution.

Results

Figure 1B:
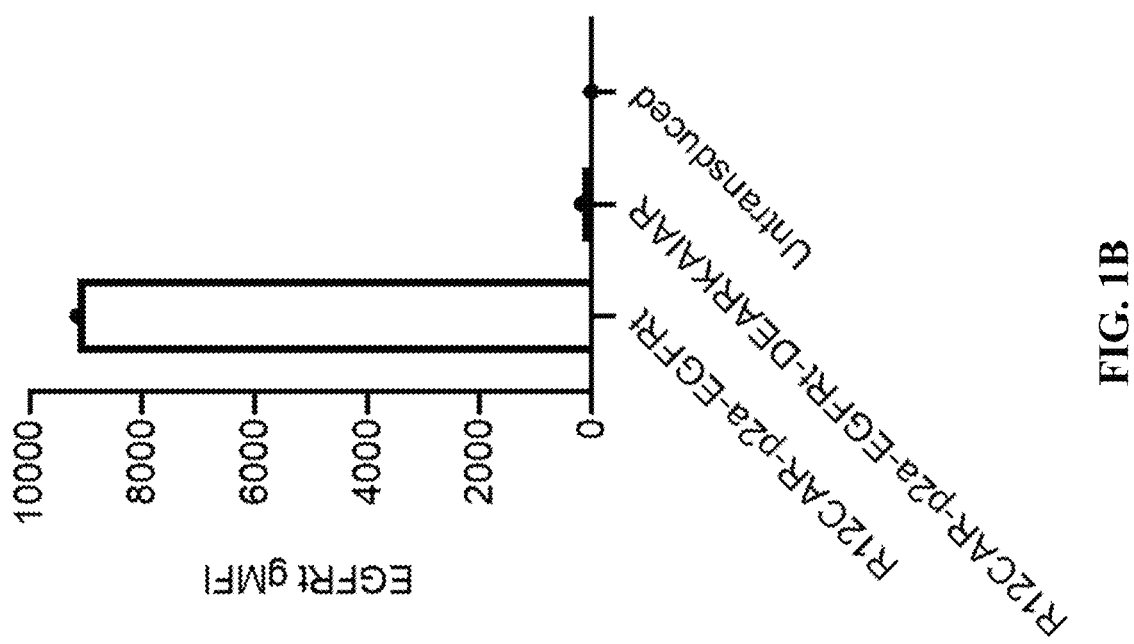

To modulate the cell surface expression of EGFRt, we fused it at the transmembrane C-terminus to a 43 amino acid synthetic sequence (DEARKAIARVKRESKRIVEDAER-LIREAAAASEKISREAERLI; SEQ ID NO:41), which contains two acidic residues (aspartic acid and glutamic acid) proximal to the membrane. We found that the cell surface detection of EGFRt was dramatically reduced as compared to EGFRt without the C-terminal fusion in transduced primary T cells (FIGS. 1A and 1B). By contrast, when we fused EGFRt at the transmembrane C-terminus to $(G_4S)_2$ (SEQ ID NO:42, where n=2), the fusion protein was detected at markedly increased (five-fold) levels at the cell surface as compared to EGFRt without the fusion ((Jurkat cells; data not shown). These data suggest that inclusion of an appropriate juxtamembrane intracellular segment could modulate the surface expression of EGFRt variants.

We hypothesized that certain amino acid compositions in the juxtamembrane intracellular region could increase EGFRt marker surface expression by enhancing membrane insertion during protein synthesis and/or improved stability of the transmembrane protein. To test this hypothesis, we generated EGFRt modules containing EGFR Domains III-IV, EGFR transmembrane domain, and short intracellular domains derived from the native EGFR sequence or synthetic sequences. Since T678 of human EGFR may be a site of regulatory phosphorylation, we selected for testing proteins containing amino acids 669-671 (RRR) or 669-677 (RRRHIVRKR; SEQ ID NO:16) (FIGS. 2A and 2B). Since glycine may disrupt α-helical structure and is enriched in the juxtamembrane region of other receptor tyrosine kinase proteins, we also tested intracellular domains containing unstructured glycine/serine-rich linkers (SGGGGSGGGGS; SEQ ID NO:13), or a short portion of the native juxtamembrane domain followed by a glycine/serine-rich linker (RRRSGGGGSGGGGS; SEQ ID NO:12). For this study, primary T cells were transduced with lentivirus expressing the ROR1-specific R12 CAR linked by a P2A skip sequence to the EGFRt variants (FIG. 3A). The expression of R12 CAR and the co-expressed EGFR-derived polypeptides was measured by flow cytometry.

The data show that, with the exception of a juxtamembrane sequence comprising membrane-proximal acidic residues (FIGS. 1A and 1B), EGFRt variants containing a juxtamembrane sequence consistently demonstrated higher mean fluorescence intensity, as compared to an EGFRt polypeptide without a juxtamembrane sequence (FIG. 3B). Notably, surface expression of the translationally linked R12 CAR was consistent for all constructs (FIG. 3B), indicating a direct impact of the juxtamembrane sequence on EGFRt stability rather than an effect on modulation of mRNA stability or translation efficiency, which would have impacted both CAR and EGFRt expression.

Figure 4A:
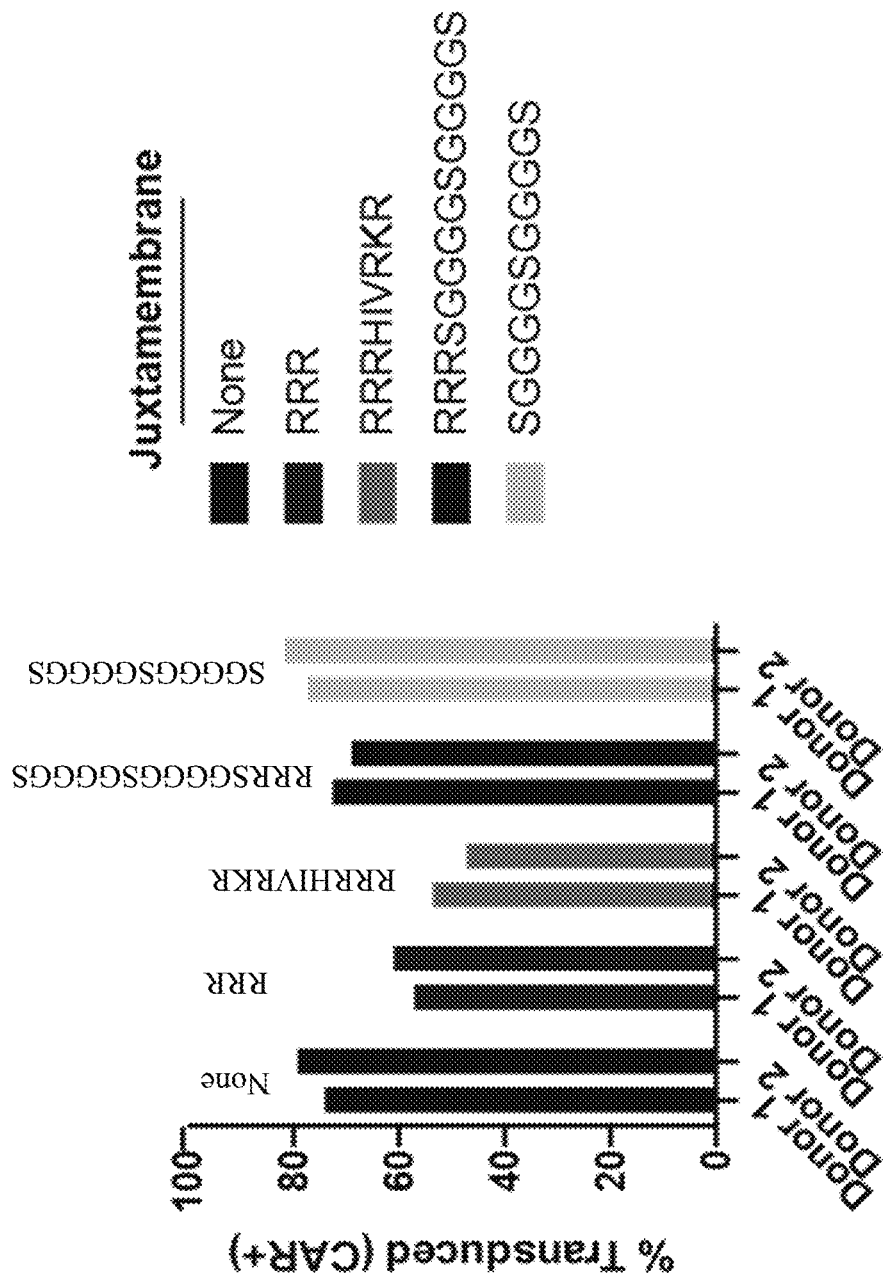
FIG. 4A is a bar graph showing the percentages of transduced T cells as indicated by R12 CAR expression. The T cells were those shown in FIGS. 3A-C. Flow cytometry was performed five days post transduction.
Figure 4B:
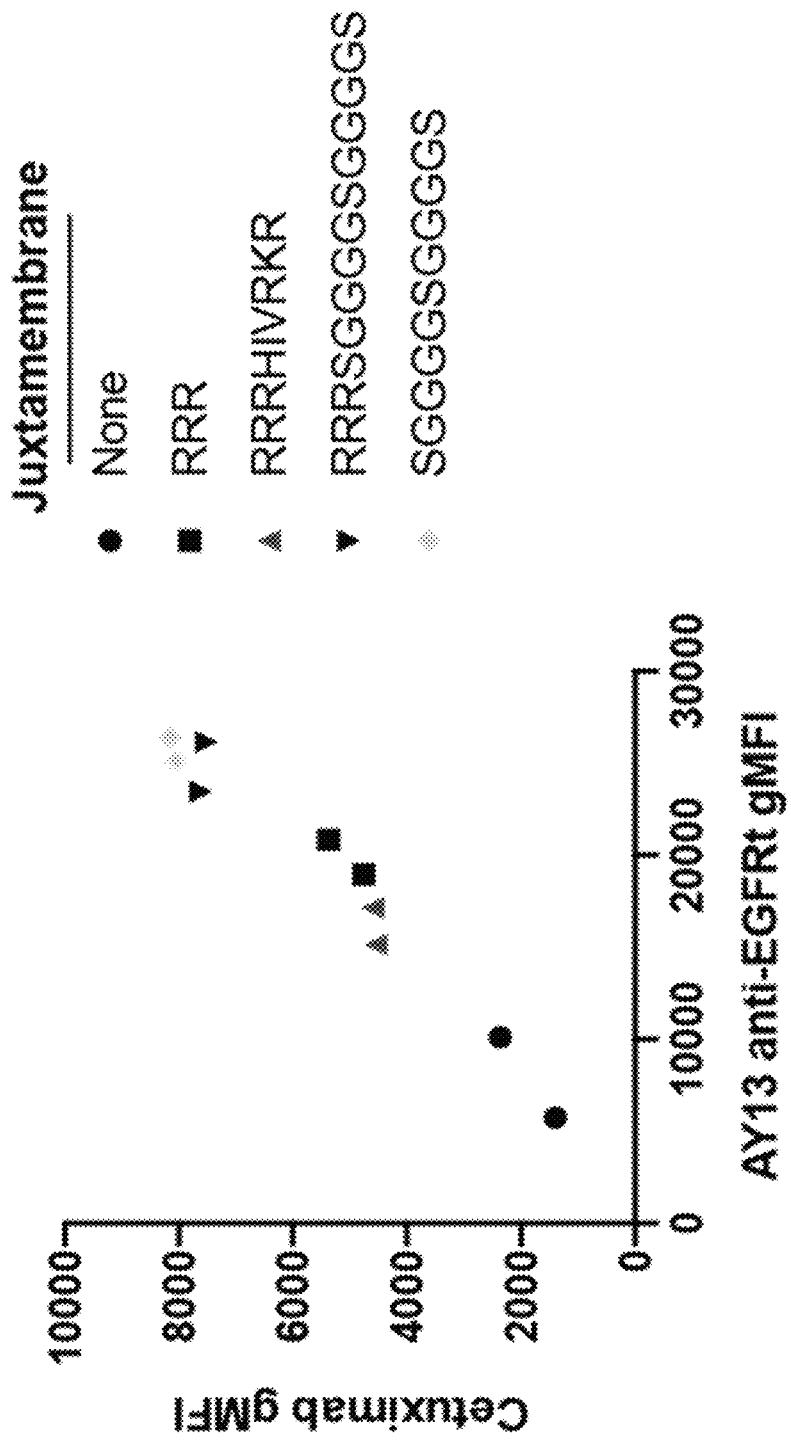
FIG. 4B is a graph showing a comparison of EGFRt detection by Domain III-specific cetuximab and Domain III-specific AY13. Flow cytometry was performed five days post transduction.
Figures 5A, 5B:
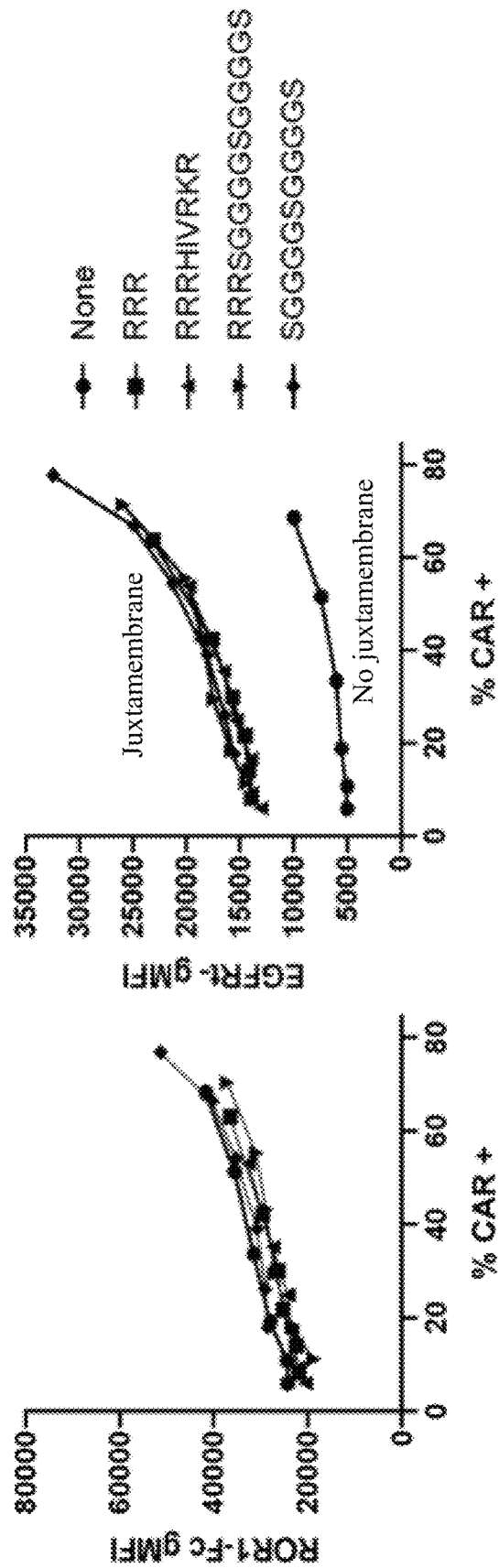
FIGS. 5A and 5B are graphs showing the effects of transduction efficiency on R12 CAR and EGFRt surface expression, respectively, in primary T cells transduced with the bi-cistronic expression constructs of FIGS. 3A-C. Flow cytometry was performed four days post transduction.

To confirm that binding of the EGFR Domain III specific AY13 monoclonal antibody accurately reflected cetuximab binding, we compared EGFRt expression levels (gMFI) determined by AY13 vs. a cetuximab biosimilar. The data demonstrated a linear relationship between gMFIs of the two antibodies and a clear increase in the cetuximab biosimilar's binding to EGFRt variants having a juxtamembrane sequence (FIGS. 4A and 4B). To investigate the role of viral copy number on EGFRt expression, we transduced primary T cells over a range of lentiviral titers. Similar to previous results, the surface gMFI of the R12 CAR was uniform across all constructs at a matching transduction frequency. In contrast, the surface gMFI of all EGFRt variants containing an intracellular sequence was about three to five-fold higher than that of the EGFRt marker lacking this sequence (FIGS. 5A and 5B). These data indicate that the presence of a suitable intracellular domain boosts the cell surface display of the EGFRt protein despite comparable translation efficiency, as measured by the expression level of the co-expressed R12 CAR. The results show that enhanced membrane insertion during protein synthesis or improved membrane protein stability plays a role in improving surface expression of the EGFR-derived proteins.

Figures 6A, 6B, 6C:
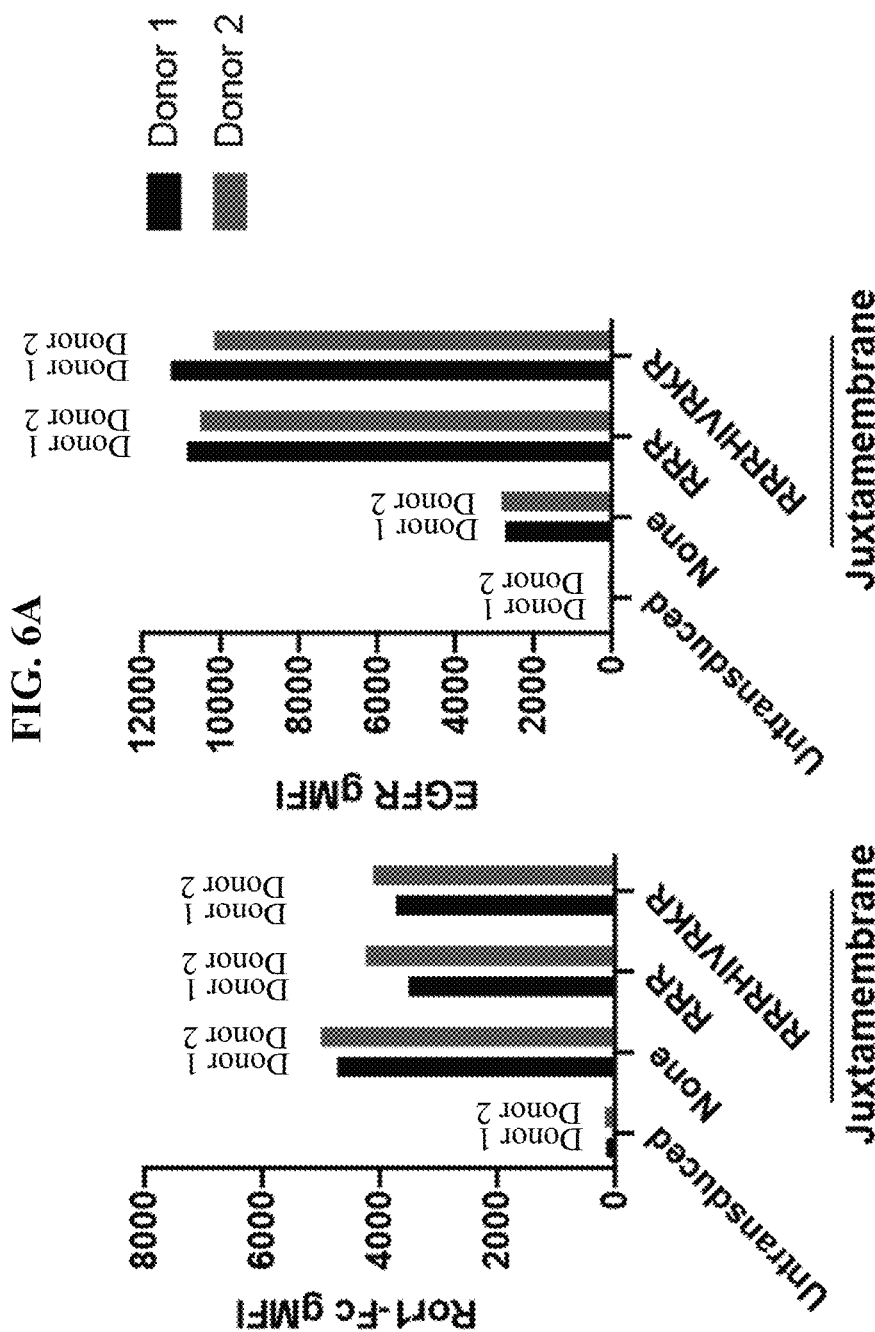
FIGS. 6A-C show the expression of a series of tri-cistronic expression constructs for EGFR-derived polypeptides in primary T cells obtained from two donors and transduced with the expression constructs.

As the number of cistronic elements in a 2A-containing expression cassette increases, there is a general pattern of decreased expression of those elements from 5' to 3', driven in part by ribosome drop-off and inefficient cleavage of 2A elements. For this reason, maximizing effective surface expression of EGFRt variants is particularly important for tri-cistronic and higher order vectors. To test the impact of juxtamembrane sequences on EGFRt expression in a tri-cistronic expression cassette, we generated lentiviral vectors comprising the c-Jun transcription factor, R12 CAR, and an EGFRt module linked by P2A skip sequences (FIG. 6A). The EGFRt modules contained either no intracellular domain or an intracellular domain comprising amino acids 669-671 or 669-677 from the human EGFR sequence. As observed for the bi-cistronic vector, R12 CAR expression was similar across all constructs. In contrast, the surface expression of EGFRt increased by about four folds with the addition of a juxtamembrane sequence (FIGS. 6B and 6C).

Example 2: Cetuximab-Mediated ADCC of CAR-T Cells Expressing EGFRt Variants

This example describes studies analyzing the efficiency of the EGFR-derived proteins described herein as a safety switch in cell therapy. Altered surface expression of EGFRt could impact the utility of this marker as a selection marker and safety switch in vivo. Cetuximab induces ADCC of tumor cells in an EGFR-dependent manner (Kimura et al., *Cancer Sci.* (2007) 98(8):1275-80). As all four juxtamembrane sequences tested induced a similar increase in surface EGFRt expression, we selected EGFRt constructs containing no juxtamembrane sequence or containing the human EGFR derived RRR and RRRHIVRKR (SEQ ID NO:16) sequences for ADCC testing.

Methods

Primary human natural killer (NK) cells were used as effector cells in ADCC assays. Natural killer cells were isolated from cryopreserved, T cell depleted (CD4−/CD8−) PBMC (AllCells) by negative selection using the EasySep Human NK Cell Kit (StemCell) according to manufacturer's protocol. To activate their cytolytic function, isolated NK cells were cultured in RPMI-10 supplemented with 10 ng/ml human IL-15 overnight before use (Wagner et al., *J Clin Invest.* (2017) 127(11):4042-58; Derer 2012, *J Immunol.* (2012) 189(11):5230-9).

Cryopreserved, transduced primary T cells were thawed and pre-cultured overnight in OpTmizer medium plus cytokines as described above. The cells were then counted, resuspended in RPMI-10, and added to a V bottom 96 well plate in a 100 μl volume and incubated with (i) a cetuximab biosimilar at the indicated final concentration, (ii) no antibody (0), or (iii) 2,000 ng/ml rituximab biosimilar (R&D Systems) for 15 minutes at 37° C. IL-15 primed NK cells were then added at a 10:1 ratio of NK:CAR-T cells and the V bottom plate was gently centrifuged (100×g, 30 sec) to bring effector and target cells together. After 4 hours of co-culture, remaining CAR+ T cells were identified by FACS. Samples were stained with anti-CD3, anti-CD56, ROR1-Fc, and FVD780, fixed, and acquired on the Ze5 cytometer under volumetric counting mode. Antibody specific ADCC of T cells was assessed by comparing the total live CD56-CD3+ ROR1-Fc+ populations treated or not treated with the antibody.

TABLE 5

| Target | Fluorochrome | Antibody | Supplier |
| --- | --- | --- | --- |
| EGFR | Alexa 488 | Hu1 (cetuximab biosimilar) | R&D systems |
| EGFR | BV421 | AY13 | BioLegend |
| CD3 | BUV805 | SK7 | Thermo Fisher |
| CD56 | PE | HCD56 | BioLegend |

Results

Figure 7:
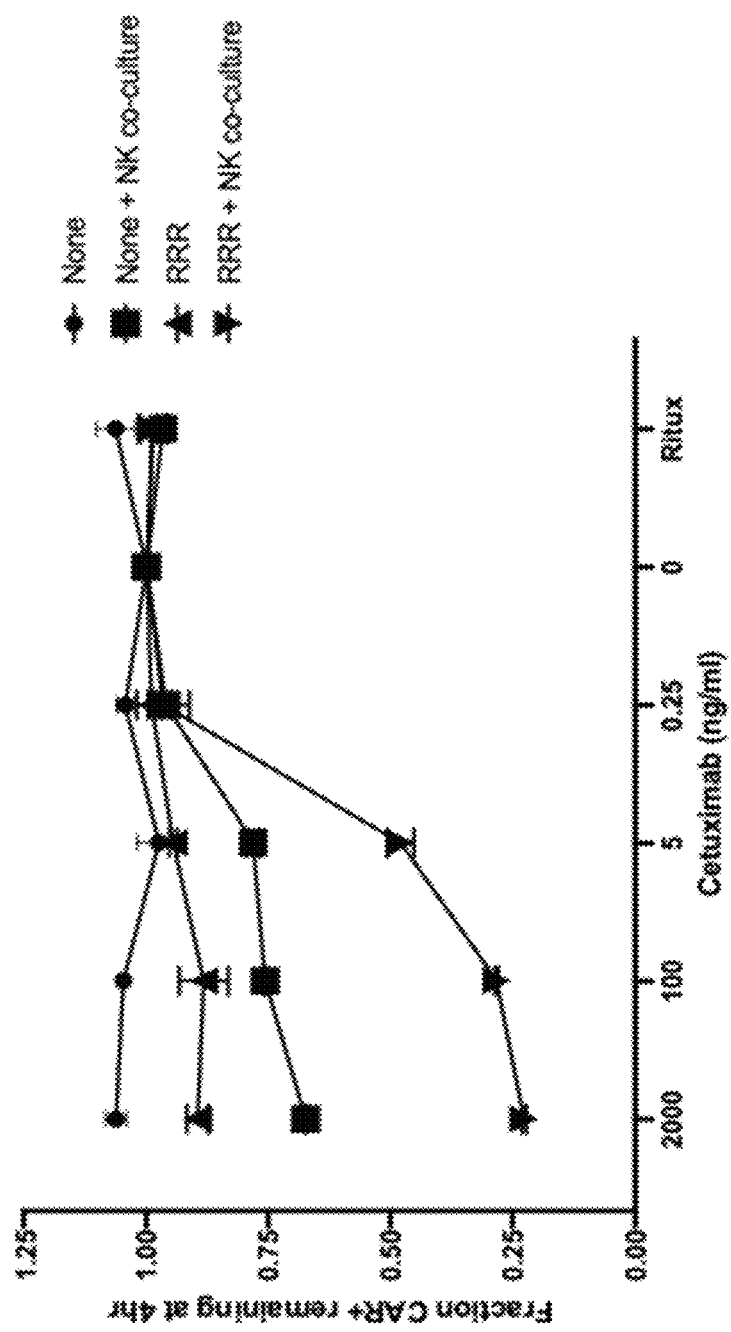
FIG. 7 shows the antibody-dependent cellular cytotoxicity (ADCC) induced by cetuximab in CAR-T cells expressing EGFR-derived polypeptides from the bi-cistronic constructs of FIG. 3A. The figure shows the fraction of CAR-T cells remaining after four hours of cetuximab treatment, relative to CAR-T cells not treated with the antibody. Ritux: rituximab.

The data show that in bi-cistronic constructs (FIG. 3A), EGFRt lacking a juxtamembrane sequence demonstrated low ADCC in the presence of NK cells and cetuximab, whereas EGFRt with a 3 amino acid RRR juxtamembrane sequence was efficiently killed in the presence of NK cells, even at cetuximab doses as low as 5 ng/ml (FIG. 7).

Figure 8:
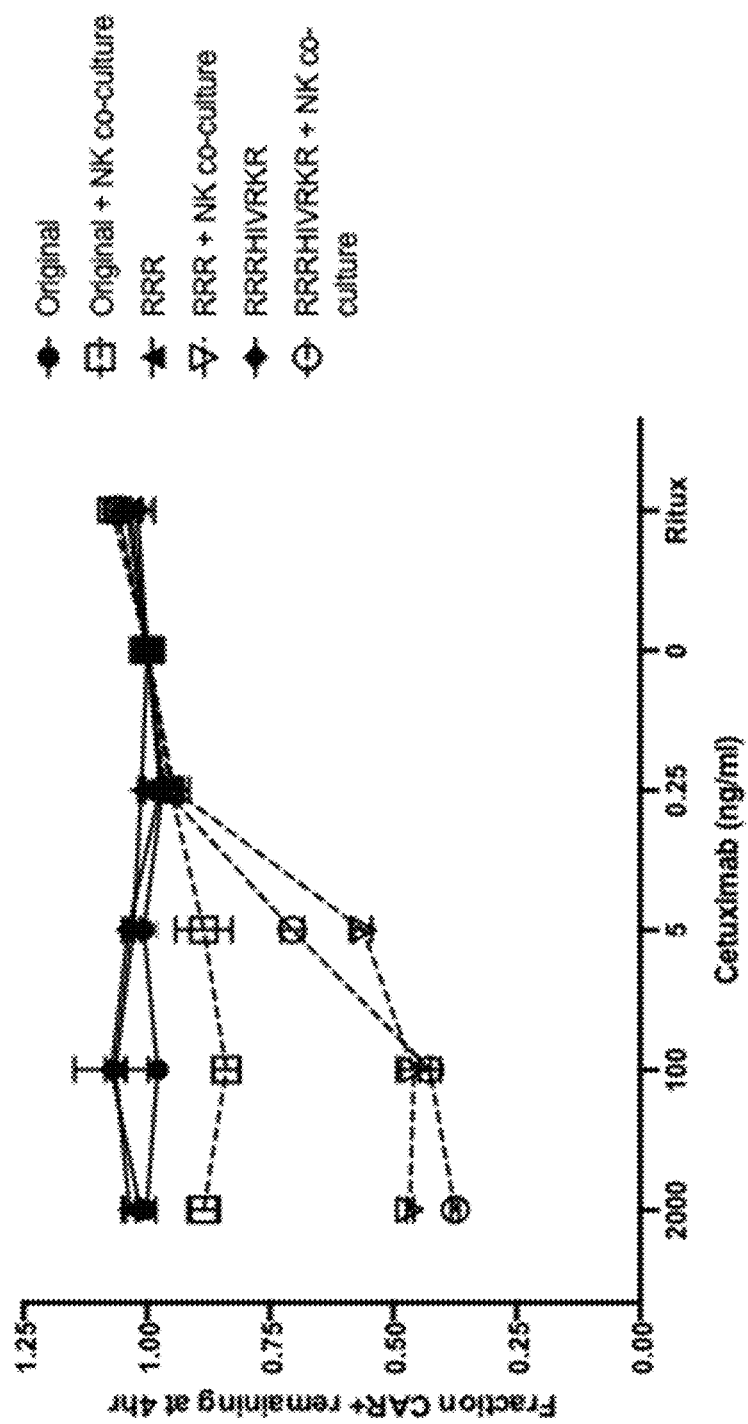
FIG. 8 is a graph showing cetuximab-induced cytotoxicity in CAR-T cells expressing EGFR-derived polypeptides from the tri-cistronic constructs of FIG. 6A. The figure shows the fraction of CAR-T cells remaining after four hours of cetuximab treatment, relative to CAR-T cells not treated with the antibody.
Figure 9:
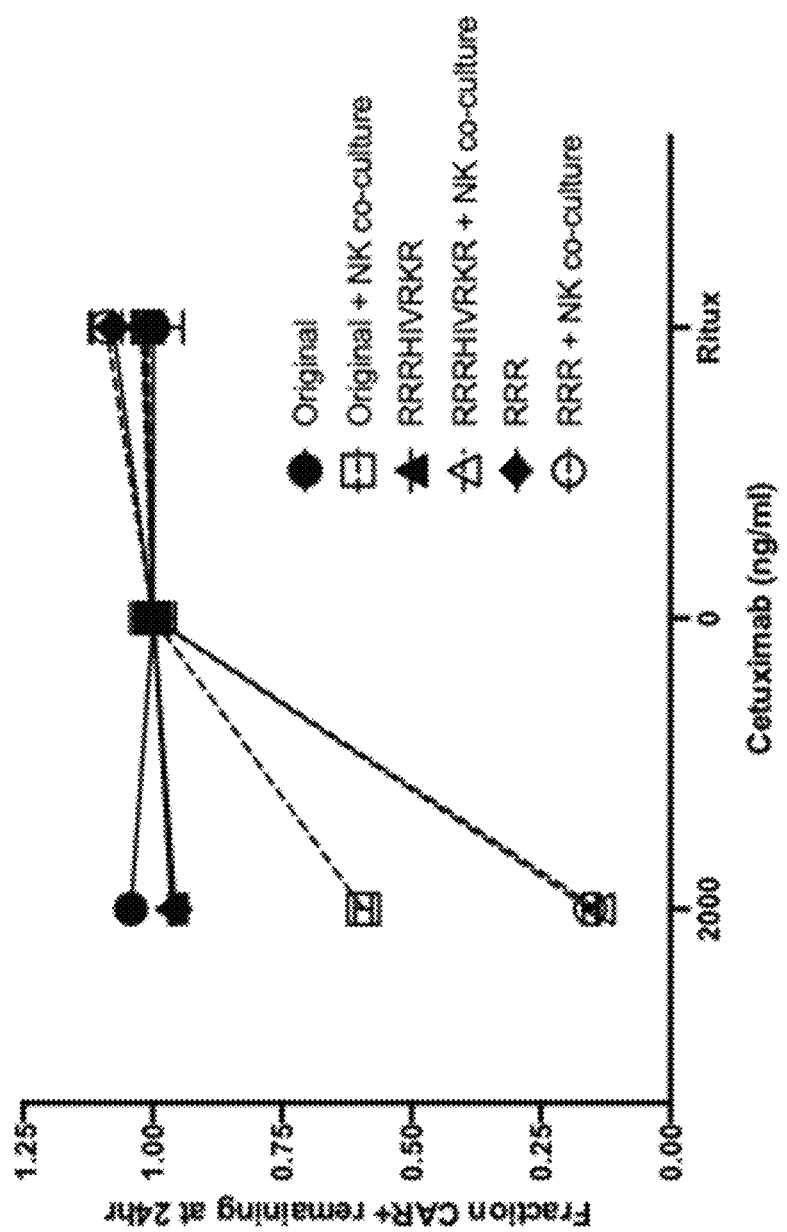
FIG. 9 shows cetuximab-induced cytotoxicity in CAR-T cells expressing EGFR-derived polypeptides from the tri-cistronic constructs of FIG. 6A. The figure shows the fraction of CAR-T cells remaining after 24 hours of cetuximab treatment, relative to CAR-T cells not treated with the antibody.

For tri-cistronic constructs with the EGFRt sequence in the 3' position (FIG. 6A), minimal ADCC was observed for EGFRt lacking a juxtamembrane sequence after 4 hours of treatment. In contrast, EGFRt with RRR or RRRHIVRKR (SEQ ID NO:16) juxtamembrane domains demonstrated significant cetuximab-mediated ADCC in a dose-dependent manner after 4 hours of treatment (FIG. 8). After 24 hours of cetuximab treatment, EGFRt lacking a juxtamembrane sequence exhibited partial ablation in a cetuximab- and NK-dependent manner, whereas EGFRt with RRR or RRRHIVRKR (SEQ ID NO:16) juxtamembrane sequences exhibited nearly complete ablation in a cetuximab- and NK-dependent manner (FIG. 9).

Example 3: Surface Expression of Additional EGFR-Derived Polypeptides

This example describes studies analyzing the effects of various short and residue-swapped juxtamembrane sequences on the cell surface expression levels of EGFR-derived polypeptides.

To test the minimal sequence requirements for maximizing cell surface expression of EGFR-derived polypeptides, tri-cistronic constructs containing coding sequences for (i) c-Jun, (ii) ROR1-specific CAR, and (iii) an EGFR-derived polypeptide were designed as described in Example 1. These tri-cistronic constructs encoded EGFRt or variants thereof having additional short juxtamembrane sequences: (i) one arginine residue (R), (ii) two arginine residues (RR), (iii) three arginine residues (RRR), or (iv) one arginine residue swapped for lysine (RKR).

Primary T cells from two different human donors were transduced with the indicated tri-cistronic constructs, or were left untransduced. Six days post transduction, cells were stained for ROR1-Fc antigen binding, EGFR expression, and fixable viability dye.

Figure 10:
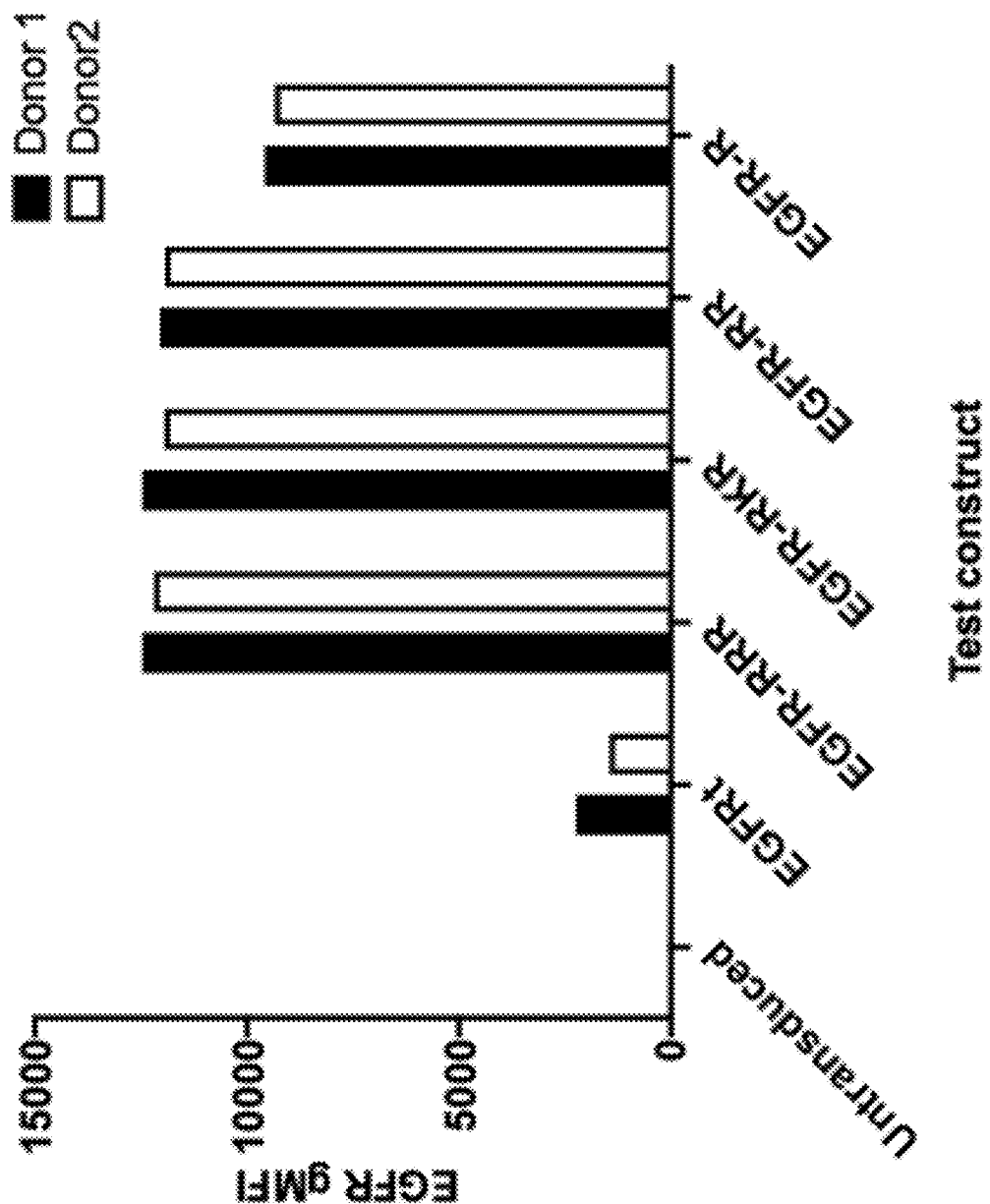
FIG. 10 is a bar graph quantitating the gMFI for anti-EGFR antibody binding in live ROR1 CAR+ cells transduced with EGFRt or variants thereof having additional intracellular juxtamembrane sequences (R, RR, RRR, or RKR) or in total live cells in the untransduced condition.

FIG. 10 shows gMFI for anti-EGFR antibody binding in ROR1 CAR+ transduced cells or total live cells in the untransduced condition. As shown in the figure, an EGFR-derived polypeptide containing the RKR juxtamembrane sequence maintained strong cell surface expression. Comparison of cell surface expression levels of EGFR-derived polypeptides containing juxtamembrane sequences with one, two, or three arginine residues (R, RR, or RRR) shows that truncation of the intracellular juxtamembrane domain from RRR to RR reduced surface expression by 2.7%. In contrast, truncation of the intracellular juxtamembrane domain from RRR to R reduced surface expression by 22%.

Example 4: Kill-Switch Function of EGFR-Derived Polypeptides In Vivo

This example describes studies assessing the effect of the juxtamembrane RRR domain on the in vivo kill-switch function of truncated EGFR following cetuximab administration.

Methods
Expression Constructs

The MP71 retroviral vector was used to generate the constructs used in these studies. The vector was modified to incorporate coding sequences for human EGFRt (MP71-EGFRt), a variant having the juxtamembrane domain RRR (MP71-EGFR-RRR), a bi-cistronic CAR expression cassette encoding the mCD19scFv.28z CAR (also annotated as m19.28z or mCD19.28z) and EGFRt or EGFR-RRR (MP71-mCD19scFv.28z.EGFRt/EGFR-RRR; also annotated herein as MP71_m19.28z.P2A.EGFRt/EGFR-RRR), or a tri-cistronic CAR expression cassette encoding c-Jun, mCD19scFv.28z, and EGFRt or EGFR-RRR (MP71-cJun.mCD19scFv.28z.EGFRt/EGFR-RRR; also annotated herein as MP71_cJun.T2A.m19.28z.P2A.EGFRt/EGFR-RRR or cJun.m19.28z.EGFRt/EGFR-RRR).

The bi-cistronic CAR constructs included a coding sequence for a CAR (mCD19.28z CAR), which included a murine CD8a signal peptide (UniProt P01731 amino acids 1-27), a murine CD19-specific scFv derived from the ID3 hybridoma (Davila et al., PLoS One (2013) 8(4):e61338), murine CD8a hinge and transmembrane regions (UniProt P01731 amino acids 151-219), a murine CD28 intracellular region (UniProt P31041 amino acids 177-218), and a murine CD3z intracellular domain (UniProt P24161 amino acids 52-164). This CAR-coding sequence was linked by a coding sequence for a P2A self-cleaving peptide sequence to the coding sequence for the human EGFR polypeptide (UniProt P00533 amino acids 334-668 for human EGFRt). For the tri-cistronic construct, a coding sequence for murine c-Jun (UniProt P05627 amino acids 1-334) was cloned upstream of the mCD19.28z CAR coding sequence and linked by a T2A peptide coding sequence.

Cell Culture, Transduction, and Adoptive Transfer

For retrovirus production, Plat-E cells (Cell Biolabs) were transiently transfected using calcium phosphate (Takara). Supernatants were collected 48 hours later, filtered through 0.45 m filters, and snap frozen on dry ice prior to storage at −80° C. C57BL/6J and B6.SJL (CD45.1) donor mice were acquired from Jackson Laboratory.

For T cell transductions, single-cell suspensions were obtained from the spleen and peripheral lymph nodes of 6- to 8-week old CD45.1 donor mice and filtered through a 40 m mesh. Murine CD8 T cells were enriched using negative selection (StemCell) and stimulated with 1 µg/ml plate-bound anti-CD3 (145-2C11) and anti-CD28 (37.51) for 20 hours at 37° C. and 5% $CO_2$ in complete RPMI (RPMI 1640, 10% heat-inactivated FBS, 1 mM HEPES, 100 U/ml penicillin/streptomycin, 1 mM sodium pyruvate, and 50 µM β-mercaptoethanol) supplemented with 50 U/ml murine IL-2 (PeproTech). Pre-titered retrovirus was loaded onto non-tissue-culture plates pre-coated with 12.5 µg/ml RetroNectin® (Takara) and captured by centrifugation for 2 hours at 2560 rcf at 32° C. Stimulated CD8+ T cells were harvested and resuspended at $1 \times 10^6$ cells/ml in complete RPMI supplemented with 50 U/ml IL-2 and anti-CD3/28 mouse T-activator Dynabeads™ (Thermo Fisher) at a 1:1 ratio. Virus-coated wells were aspirated and rinsed with PBS, followed by addition of the T cells, centrifugation at 800 rcf for 30 min at 32° C., and incubation at 37° C. in 5% $CO_2$.

After 24 hours, IL-2-supplemented complete RPMI media was replaced, and T cells were incubated for an additional 24 hours. T cells were harvested, resuspended at $1 \times 10^6$ cells/ml in complete RPMI supplemented with 50 U/ml murine IL-15 (PeproTech), and incubated for an additional 48 hours. Magnetic activator beads were subsequently removed and T cell transduction efficiency (40-60% EGFR$^+$) was confirmed by flow cytometry. Transduced cells were then prepared for adoptive transfer by resuspending CD8' T cells at $3 \times 10^6$ EGFR$^+$/100 µl in serum-free RPMI 1640 and kept on ice prior to adoptive transfer.

For CAR-T cell adoptive transfer, 6- to 8-week old C57BL/6J mice were pre-conditioned with intraperitoneal injection of 200 mg/kg cyclophosphamide and were injected intravenously by retro-orbital injection with $3 \times 10^6$ EGFR$^+$ CAR-T cells after 6 hours. For analysis of peripheral blood, 100 µl blood samples were collected by retro-orbital bleeding into EDTA-coated tubes on the indicated days post CAR-T cell transfer and the blood samples were treated with two rounds of ACK lysis buffer prior to surface staining. Samples were stained using LIVE/DEAD™ Fixable Aqua Dead Cell stain kit (Invitrogen) at 4° C. for 15 minutes. Cells were also stained in the dark at 4° C. for 30 minutes in flow buffer (PBS, 1 mM EDTA, and 2% FBS) with anti-CD8a FITC (53-6.7, BioLegend unless stated otherwise), anti-CD19 PerCP-Cy™ 5.5 (1D3), anti-CD4 PE-Cy™ 7 (RM4-5), anti-CD45.2 APC/Fire™ 750 (104), anti-CD45.1 Brilliant Violet 421™ (A20), hEGFR APC or PE (AY13), and acquired on BD FACSCelesta™ cell analyzer.

For depletion of transferred EGFR+ CAR-T cells, cetuximab was infused at 1 mg or 0.1 mg per mouse on day 8. Expansion and depletion of CAR-T cells were monitored in blood samples by flow cytometry. The mice were shown to exhibit B-cell aplasia when the frequency of CD19+ B cells was maintained below 3% of the total circulating endogenous $CD45.2^+$ cells.

Results

EGFR-RRR Exhibits Superior Surface Expression Levels in the Infusion Product

Figure 11A:
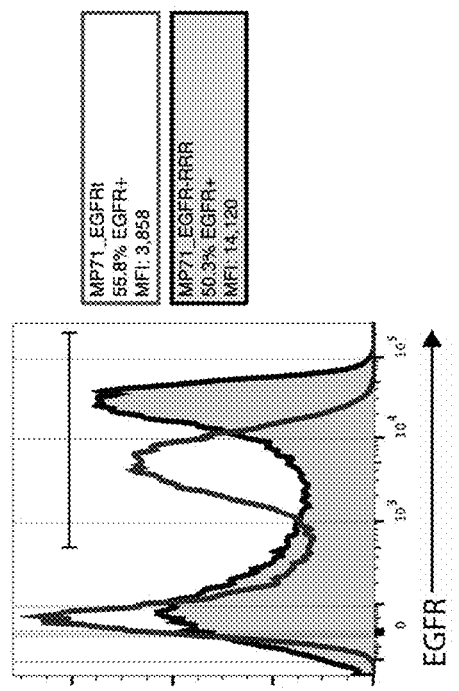
FIGS. 11A and 11B show surface expression levels of EGFRt (white) or EGFR-RRR (EGFRt with an RRR juxtamembrane domain; grey) in mouse T cells transduced with MP71 retroviral constructs that were mono-cistronic (FIG. 11A) or bi-cistronic (FIG. 11B). MFI: mean fluorescence intensity.

To assess the effect of juxtamembrane modification on the surface expression of truncated EGFR in vitro, murine CD8+ T cells were transduced with a retroviral construct comprising the mouse-codon-optimized sequence of human EGFRt with or without an RRR juxtamembrane domain, and analyzed by flow cytometry as described previously. When CD8+ T cells were transduced at similar levels (50-56%), $EGFR^+$ T cells exhibited >3-fold increase in EGFR-RRR surface expression compared to EGFRt (FIG. 11A).

Figure 11B:
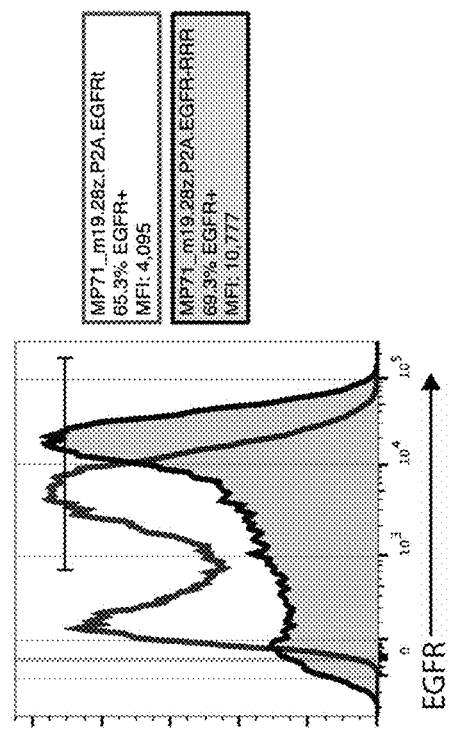

To determine the effect of the juxtamembrane domain in the context of a multi-cistronic construct, a coding sequence for an EGFR polypeptide was linked by a coding sequence for a P2A self-cleaving peptide to the 3' end of a coding sequence for a CAR targeting mouse CD19. At similar transduction efficiencies, CAR-T cells transduced with the EGFR-RRR construct displayed high levels of EGFR staining than CAR-T cells transduced with the EGFRt construct (FIG. 11B). Thus, when surface expression is measured by flow cytometry in T cell samples with similar transduction levels, EGFR-RRR exhibited increased surface expression levels on the CAR T cell infusion product.

EGFR-RRR is a Stable Target for Antibody-Mediated Depletion In Vivo

Figure 12A:
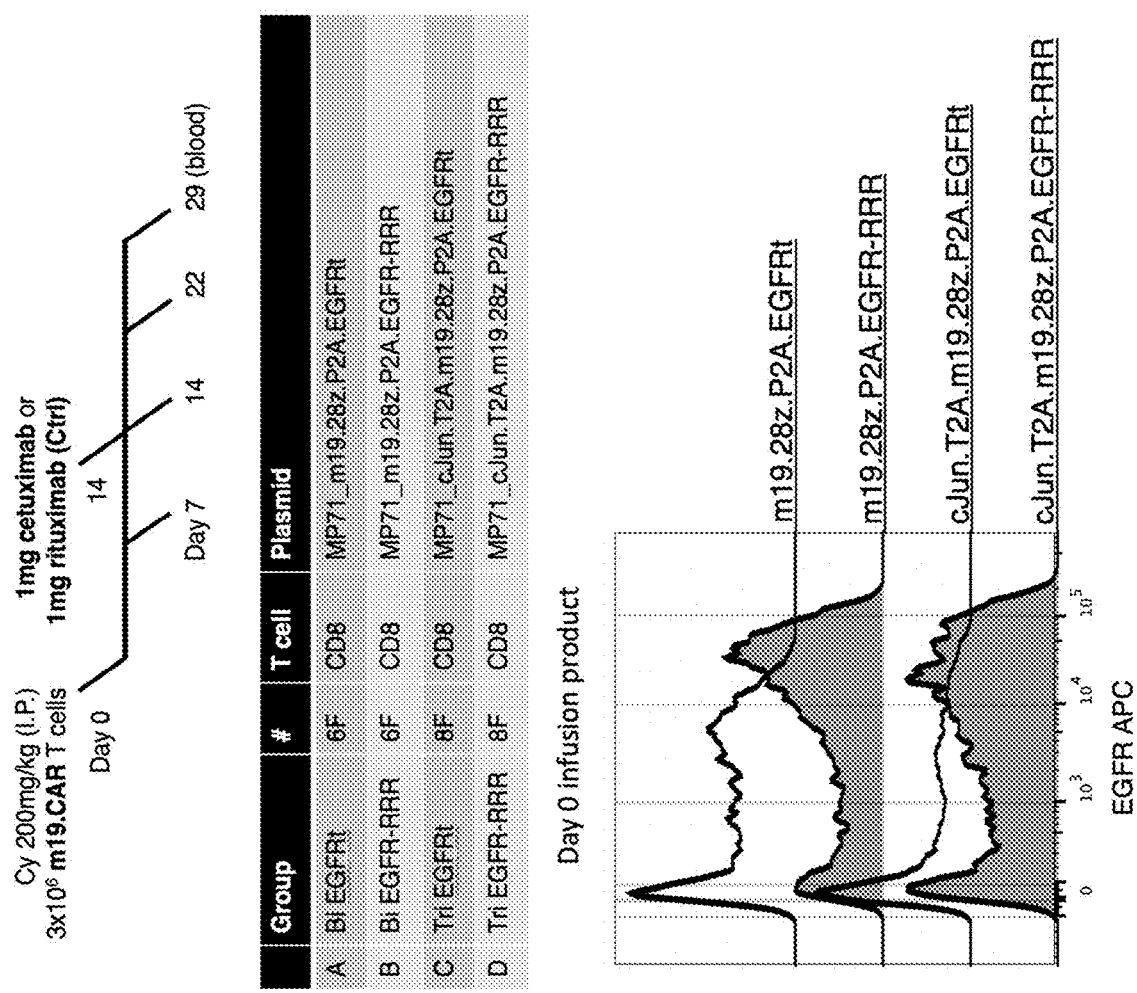
FIG. 12A shows a schematic (top panel) of an in vivo study on the indicated CAR-T infusion products (middle panel) and expression levels of the EGFR polypeptides EGFRt or EGFR-RRR (bottom panel).

Stably expressed EGFRt can be targeted for depletion with the EGFR-targeting antibody cetuximab (Paszkiewicz et al., *J Clin Invest.* (2016) 126(11):4262-72). To assess whether EGFR-RRR surface expression is maintained and can be targeted for depletion in vivo, EGFRt or EGFR-RRR were expressed in a bi-cistronic (downstream of mCD19 CAR) or tri-cistronic construct (downstream of cJun.mCD19 CAR) on congenically marked CD45.1+ donor CD8+ T cells. The data show that EGFR-RRR exhibited higher levels of surface expression in the infusion product (FIG. 12A, bottom). Bulk T cell infusions containing $3\times10^6$ $EGFR^+$ CAR-T cells were adoptively transferred into lymphodepleted mice. Circulating CAR-T cell levels were tracked in the blood as indicated (FIG. 12A, top). $EGFR^+$ CAR-T cells underwent an expansion peak one to two weeks post infusion and declined thereafter.

Figure 12B:
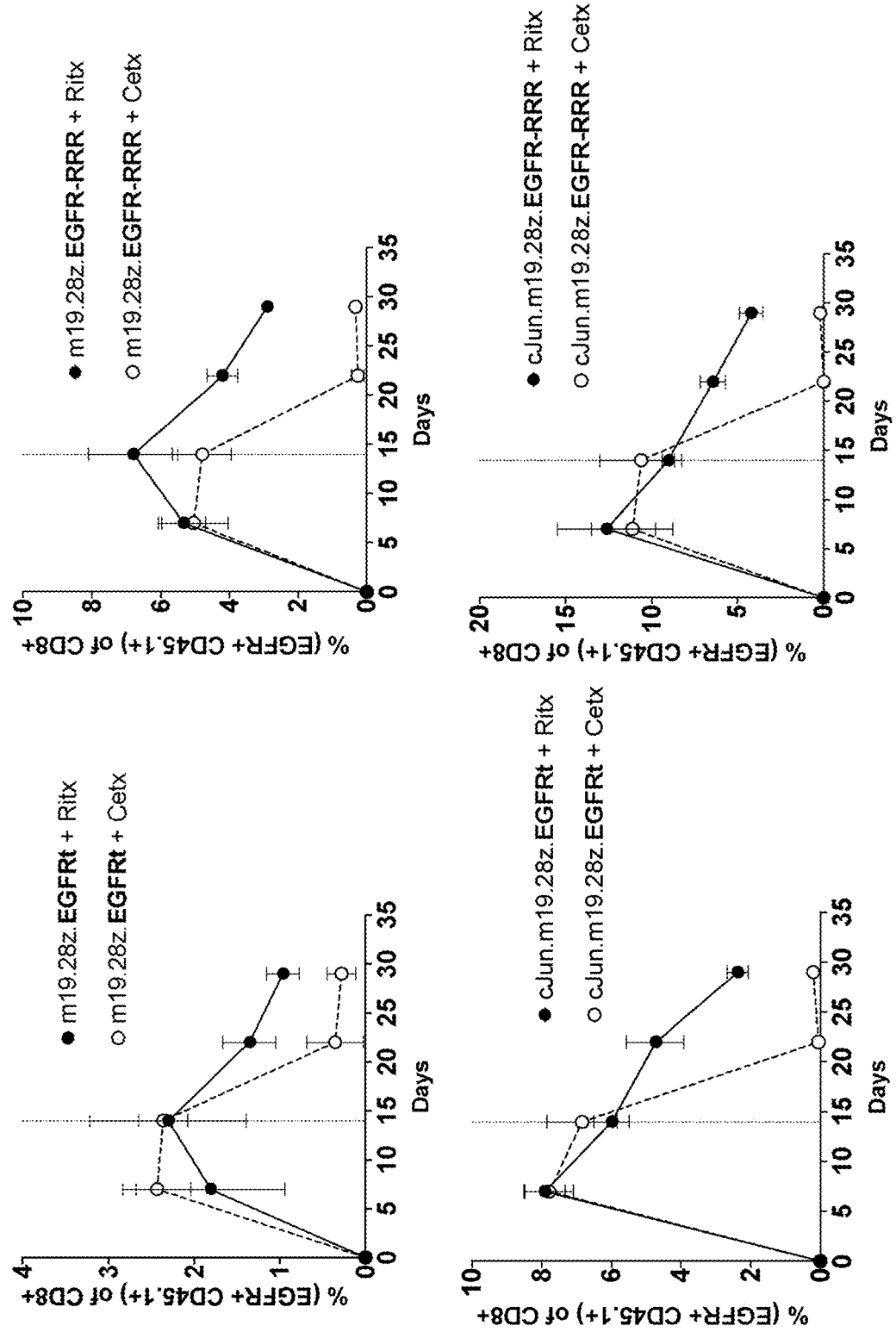
FIG. 12B is a panel of graphs showing the kinetics of circulating EGFRt and EGFR-RRR CAR-T cells following cetuximab (Cetx) treatment (white circle) compared to rituximab (control; Ritx) (black circle). Grey line represents depletion time point.
Figure 12C:
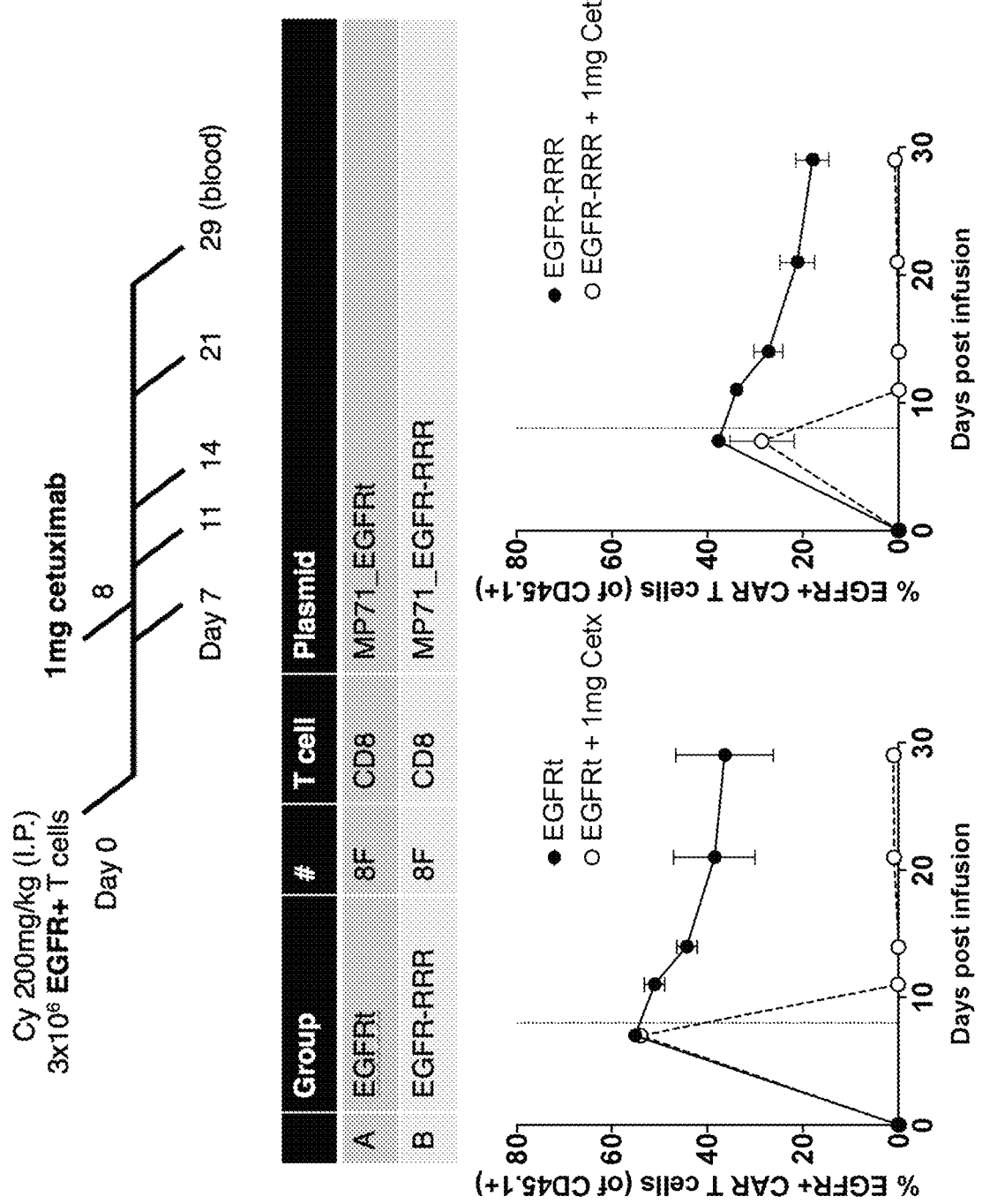
FIG. 12C shows the results of an in vivo study on the depletion kinetics of circulating EGFRt and EGFR-RRR transduced T cells. Top panel: a schematic showing the adoptive transfer of EGFR+ T cells. Bottom panel: graphs showing kinetics of circulating EGFR+ T cells following treatment with cetuximab (white circle). Grey line represents depletion time point.

To confirm that EGFR-RRR can be targeted for depletion, on day 14, half of the mice in each cohort were administered 1 mg of cetuximab or 1 mg of rituximab (control). Following injection, cetuximab depleted a large fraction of EGFRt and EGFR-RRR CAR-T cells, while CAR-T cells were maintained at higher levels in the rituximab cohorts during the observation period (FIG. 12B). Similar depletion results were obtained when T cells expressed EGFRt or EGFR-RRR without CAR (FIG. 12C). These results demonstrate that EGFR-RRR surface expression levels were maintained in vivo and could be efficiently targeted for depletion with cetuximab.

Figure 13A:
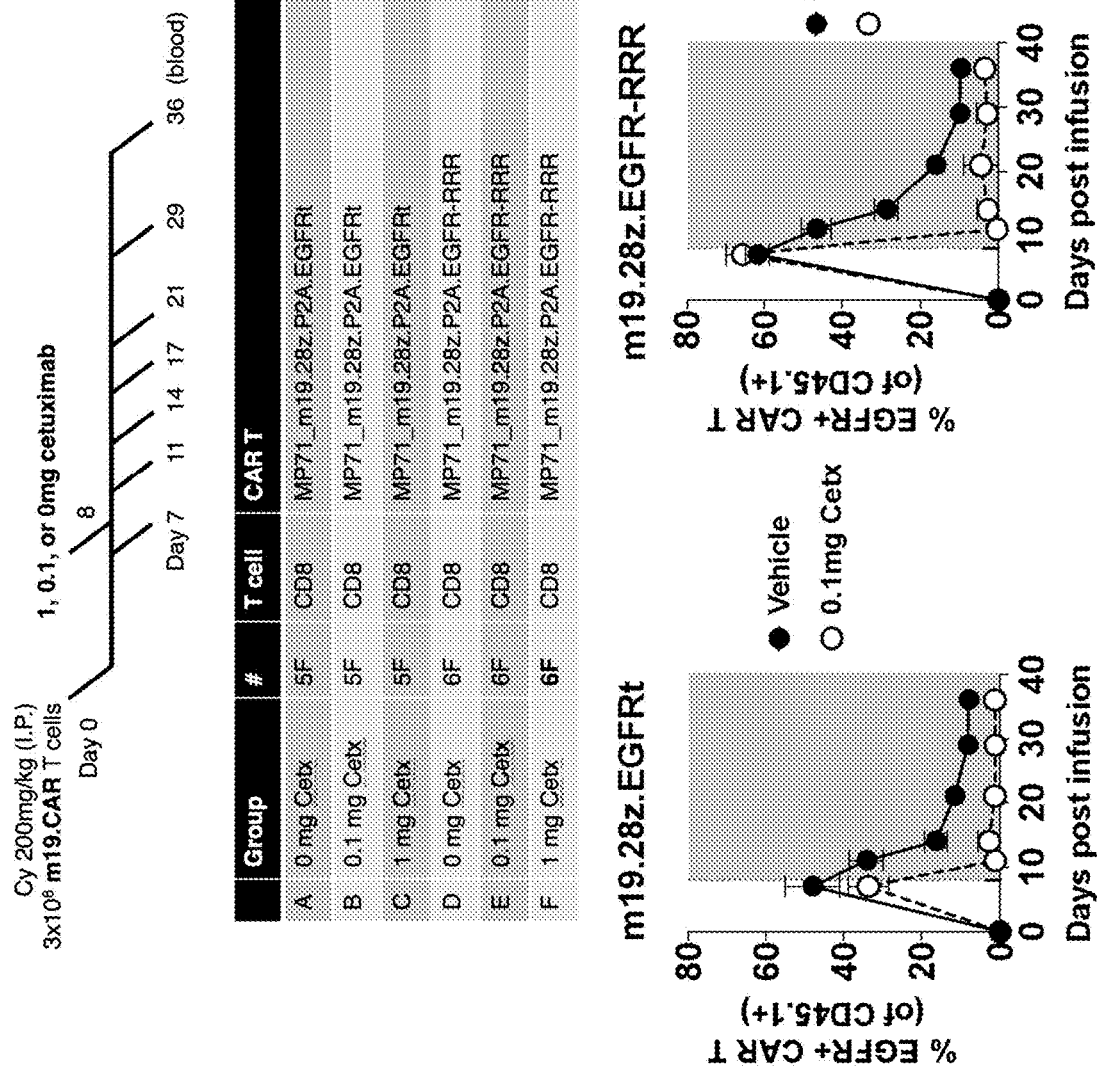
FIG. 13A shows the results of an in vivo study on the depletion kinetics of circulating EGFRt (left) and EGFR-RRR (right) CAR-T cells following treatment with cetuximab (white circle) or vehicle (black circle). Shaded area represents post-depletion window.

EGFR-RRR Mediates More Rapid Rebound of B Cells Following T Cell Depletion by Cetuximab As the addition of the juxtamembrane domain increased EGFR surface levels, we next determined whether EGFR-RRR exhibits differential CAR-T cell depletion kinetics and functional outcomes in vivo. To that end, congenically marked mCD19.28z CAR-T cells expressing EGFRt or EGFR-RRR were adoptively transferred into lymphodepleted mice. T cell engraftment and B cell aplasia were tracked in the blood over time (FIG. 13A). To elucidate differences in the depletion kinetics between EGFRt and EGFR-RRR mCD19.28z CAR T cells, a dose titration of cetuximab was performed. Targeting EGFR for depletion with a single dose of 0.1 mg cetuximab was sufficient to deplete circulating EGFRt and EGFR-RRR CAR-T cells three days following antibody injection. Expression levels of surface EGFR have previously been shown to determine the depletion kinetics of mCD19.28z CAR T cells in vivo (Paszkiewicz et al., 2016). To determine whether EGFR-RRR can mediate more rapid kinetics of B cell rebound post cetuximab, circulating B cells were tracked in mice that received mCD19.28z CAR T cells with or without subsequent depletion. Whereas mice treated with mCD19.28z CAR T cells exhibited sustained B cell aplasia, B cells in cetuximab-treated mice rebounded within 3 weeks of antibody administration. Cetuximab administration in mice previously infused with EGFR-RRR CAR-T cells resulted in more rapid rebound of B cells, including at the lower administered dose (FIG. 13B), and a more rapid resolution of B cell aplasia (FIG. 13C). Therefore, EGFR-RRR mediates more efficient depletion of CAR-T cells, resulting in more rapid shutdown kinetics of the CAR-T cell response following cetuximab.

In summary, mCD19.28z.EGFR-RRR CAR-T cells exhibit higher expression levels of EGFR. This expression was maintained in vivo and was efficiently targeted for depletion with cetuximab. In contrast to EGFRt, targeting EGFR-RRR with cetuximab resulted in complete depletion of mCD19.28z.CAR T cells and more rapid rebound of B cells in vivo.

The invention claimed is:

1. A nucleic acid molecule comprising a coding sequence for a recombinant polypeptide comprising an extracellular region, a transmembrane region, and an intracellular region, wherein
the extracellular region comprises a human epidermal growth factor receptor (EGFR) Domain III sequence and does not comprise EGFR Domain I or II, and
the intracellular region (i) comprises a juxtamembrane domain that is net-neutral or net-positively charged in the first at least three amino acids (ii) but lacks an EGFR tyrosine kinase domain.

2. A cell comprising the nucleic acid molecule of claim 1.

3. The cell of claim 2, wherein the cell is a human T cell.

4. A pharmaceutical composition comprising the nucleic acid molecule of claim 1, or a recombinant virion comprising the nucleic acid molecule of claim 1, or a cell comprising the nucleic acid molecule of claim 1; and a pharmaceutically acceptable carrier.

5. A method of making a genetically engineered human cell, comprising providing an isolated human cell, and introducing the nucleic acid molecule of claim 1 into the human cell.

6. The method of claim 5, wherein the human cell is a human T cell.

7. The nucleic acid molecule of claim 1, wherein more than half of the amino acids of the juxtamembrane domain are glycine, serine, arginine, lysine, threonine, asparagine, glutamine, aspartic acid, glutamic acid, tyrosine, tryptophan, histidine, and/or proline.

8. The nucleic acid molecule of claim 1, wherein the juxtamembrane domain comprises amino acids selected according to the table below at the indicated positions:

| Position | Amino Acid |
| --- | --- |
| 1 | R, K, C, L, H, S, N, A, Y, F, M, W, G, T, or Q |
| 2 | R, K, C, G, L, Q, I, Y, F, M, N, S, T, W, or H |
| 3 | R, K, L, C, M, W, Y, I, N, V, T, Q, A, F, G, S, D, E, or H |
| 4 | R, K, H, Q, G, S, C, N, V, W, P, F, T, D, E, or Y |
| 5 | R, K, Q, C, G, A, I, L, N, P, T, W, S, D, E, Y, or H |
| 6 | K, R, Q, P, V, D, N, Y, I, E, C, A, H, W, G, F, S, or T |
| 7 | K, R, or another amino acid |
| 8 | K, R, S, Q, G, L, I, T, P, Y, N, A, F, W, D, H, or E |
| 9 | K, R, G, L, Y, E, F, Q, S, A, H, P, T, N, D, or W |
| 10 | G, A, E, R, D, K, T, Y, V, F, S, M, Q, L, N, P, W, or H |
| 11 | K, R, Q, S, A, E, L, T, P, N, I, D, F, G, V, Y, W, or H |
| 13 | S, E, R, F, K, P, L, Y, D, or another amino acid |
| 14 | T, R, S, E, A, P, Q, K, N, V, or another amino acid |
| 15 | D, E, S, L, P, A, R, V, M, or another amino acid |
| 16 | E, V, Q, A, or another amino acid |

-continued

| Position | Amino Acid |
|---|---|
| 17 | E, L, D, Q, V, A, K, or another amino acid |
| 20 | E, G, L, R, S, V, Y, K, D, or another amino acid. |

9. The nucleic acid molecule of claim 1, wherein the juxtamembrane domain comprises RRRHIVRKR (SEQ ID NO: 16), RRRHIVRK (SEQ ID NO: 17), RRRHIVR (SEQ ID NO: 18), RRRHIV (SEQ ID NO: 19), RRRHI (SEQ ID NO:20), RRRH (SEQ ID NO:21), RRR, RKR, or RR.

10. The nucleic acid molecule of claim 1, wherein the intracellular region does not contain any residue that is phosphorylated.

11. The nucleic acid molecule of claim 1, wherein the Domain III sequence comprises SEQ ID NO:2.

12. The nucleic acid molecule of claim 1, wherein the extracellular region further comprises, C-terminal to the Domain III sequence, (i) a sequence derived from EGFR Domain IV, (ii) an artificial sequence, or (iii) both (i) and (ii).

13. The nucleic acid molecule of claim 12, wherein the extracellular region comprises amino acids 334-504, 334-525, or 334-645 of SEQ ID NO:1.

14. The nucleic acid molecule of claim 1, wherein the transmembrane region is derived from a human EGFR transmembrane domain.

15. The nucleic acid molecule of claim 14, wherein the transmembrane region comprises SEQ ID NO:5.

16. The nucleic acid molecule of claim 1, wherein the recombinant polypeptide further comprises a signal peptide derived from human EGFR, human granulocyte-macrophage colony-stimulating factor (GM-CSF), human Ig kappa, mouse Ig kappa, or human CD33.

17. The nucleic acid molecule of claim 1, wherein the recombinant polypeptide comprises SEQ ID NO:26, 27, 28, 29, 30, 31, 32, 33, 34, 35, 36, 37, 38, 39, or 40.

18. The nucleic acid molecule of claim 1, further comprising a coding sequence for a chimeric antigen receptor (CAR).

19. The nucleic acid molecule of claim 18, wherein the CAR is specific for a tumor antigen.

20. The nucleic acid molecule of claim 18, wherein the coding sequences for the recombinant polypeptide and the CAR are operably linked to the same promoter such that the two coding sequences are co-transcribed.

21. The nucleic acid molecule of claim 20, wherein the two coding sequences are separated by (i) an internal ribosome entry site (IRES) or (ii) a coding sequence for a self-cleaving peptide wherein the coding sequences for the recombinant polypeptide, the CAR, and the self-cleaving peptide are in frame with each other.

22. The nucleic acid molecule of claim 18, further comprising a coding sequence for a third polypeptide.

23. The nucleic acid molecule of claim 22, wherein the coding sequences for the recombinant polypeptide, the CAR, and the third polypeptide are operably linked to the same promoter such that the three coding sequences are co-transcribed.

24. The nucleic acid molecule of claim 22, wherein the three coding sequences are separated from each other by (i) an internal ribosome entry site (IRES) or (ii) a coding sequence for a self-cleaving peptide wherein the coding sequences for the recombinant polypeptide, the CAR, the third polypeptide, and the self-cleaving peptide(s) are in frame with each other.

25. The nucleic acid molecule of claim 24, wherein
the promoter is a constitutive or inducible promoter,
the self-cleaving peptide is a 2A peptide, and/or
the CAR is specific for a tumor antigen.

26. The nucleic acid molecule of claim 25, wherein the promoter is an MND promoter.

27. The nucleic acid molecule of claim 1, wherein the nucleic acid molecule is a viral vector.

28. The nucleic acid molecule of claim 27, wherein the viral vector is a lentiviral vector.

* * * * *

SEQUENCE LISTING

```
<160> NUMBER OF SEQ ID NOS: 47

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15
```

```
Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430
```

```
His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
```

```
                    850                 855                 860
Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                    885                 890                 895

Val Trp Ser Tyr Gly Val Thr Val Trp Glu Leu Met Thr Phe Gly Ser
                    900                 905                 910

Lys Pro Tyr Asp Gly Ile Pro Ala Ser Glu Ile Ser Ser Ile Leu Glu
                    915                 920                 925

Lys Gly Glu Arg Leu Pro Gln Pro Pro Ile Cys Thr Ile Asp Val Tyr
                    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                    965                 970                 975

Arg Tyr Leu Val Ile Gln Gly Asp Glu Arg Met His Leu Pro Ser Pro
                    980                 985                 990

Thr Asp Ser Asn Phe Tyr Arg Ala Leu Met Asp Glu Glu Asp Met Asp
                    995                 1000                1005

Asp Val Val Asp Ala Asp Glu Tyr Leu Ile Pro Gln Gln Gly Phe
                1010                1015                1020

Phe Ser Ser Pro Ser Thr Ser Arg Thr Pro Leu Leu Ser Ser Leu
                1025                1030                1035

Ser Ala Thr Ser Asn Asn Ser Thr Val Ala Cys Ile Asp Arg Asn
                1040                1045                1050

Gly Leu Gln Ser Cys Pro Ile Lys Glu Asp Ser Phe Leu Gln Arg
                1055                1060                1065

Tyr Ser Ser Asp Pro Thr Gly Ala Leu Thr Glu Asp Ser Ile Asp
                1070                1075                1080

Asp Thr Phe Leu Pro Val Pro Glu Tyr Ile Asn Gln Ser Val Pro
                1085                1090                1095

Lys Arg Pro Ala Gly Ser Val Gln Asn Pro Val Tyr His Asn Gln
                1100                1105                1110

Pro Leu Asn Pro Ala Pro Ser Arg Asp Pro His Tyr Gln Asp Pro
                1115                1120                1125

His Ser Thr Ala Val Gly Asn Pro Glu Tyr Leu Asn Thr Val Gln
                1130                1135                1140

Pro Thr Cys Val Asn Ser Thr Phe Asp Ser Pro Ala His Trp Ala
                1145                1150                1155

Gln Lys Gly Ser His Gln Ile Ser Leu Asp Asn Pro Asp Tyr Gln
                1160                1165                1170

Gln Asp Phe Phe Pro Lys Glu Ala Lys Pro Asn Gly Ile Phe Lys
                1175                1180                1185

Gly Ser Thr Ala Glu Asn Ala Glu Tyr Leu Arg Val Ala Pro Gln
                1190                1195                1200

Ser Ser Glu Phe Ile Gly Ala
                1205                1210

<210> SEQ ID NO 2
<211> LENGTH: 171
<212> TYPE: PRT
<213> ORGANISM: Homo sapiens

<400> SEQUENCE: 2
```

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
                35                  40                  45

Thr His Thr Pro Pro Leu Asp Pro Gln Glu Leu Asp Ile Leu Lys Thr
            50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
        130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln
                165                 170

<210> SEQ ID NO 3
<211> LENGTH: 141
<212> TYPE: PRT
<213> ORGANISM: Homo sapiens

<400> SEQUENCE: 3

Val Cys His Ala Leu Cys Ser Pro Glu Gly Cys Trp Gly Pro Glu Pro
1               5                   10                  15

Arg Asp Cys Val Ser Cys Arg Asn Val Ser Arg Gly Arg Glu Cys Val
                20                  25                  30

Asp Lys Cys Asn Leu Leu Glu Gly Glu Pro Arg Glu Phe Val Glu Asn
                35                  40                  45

Ser Glu Cys Ile Gln Cys His Pro Glu Cys Leu Pro Gln Ala Met Asn
            50                  55                  60

Ile Thr Cys Thr Gly Arg Gly Pro Asp Asn Cys Ile Gln Cys Ala His
65                  70                  75                  80

Tyr Ile Asp Gly Pro His Cys Val Lys Thr Cys Pro Ala Gly Val Met
                85                  90                  95

Gly Glu Asn Asn Thr Leu Val Trp Lys Tyr Ala Asp Ala Gly His Val
            100                 105                 110

Cys His Leu Cys His Pro Asn Cys Thr Tyr Gly Cys Thr Gly Pro Gly
            115                 120                 125

Leu Glu Gly Cys Pro Thr Asn Gly Pro Lys Ile Pro Ser
        130                 135                 140

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Val Thr Gly Ser Gly Trp Gly Pro Glu Pro Gly Gly Gly Ser
1               5                   10

<210> SEQ ID NO 5
<211> LENGTH: 23
<212> TYPE: PRT
<213> ORGANISM: Homo sapiens

<400> SEQUENCE: 5

Ile Ala Thr Gly Met Val Gly Ala Leu Leu Leu Leu Val Val Ala
1               5                   10                  15

Leu Gly Ile Gly Leu Phe Met
            20

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ser Gly Ser Gly Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Arg Ser Asp
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Arg Ser Asp Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Gly Gly Gly
1               5

<210> SEQ ID NO 10
<211> LENGTH: 5
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 10

Ser Gly Ala Gly Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Arg Ala Asp Lys
1               5

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg Arg Ser Gly Gly Gly Gly Ser Gly Gly Gly Gly Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Gly Gly Gly Ser Gly Gly Gly Gly Ser
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 14

Gly Gly Gly Gly Ser
1               5

<210> SEQ ID NO 15
<211> LENGTH: 35
<212> TYPE: PRT
<213> ORGANISM: Homo sapiens

<400> SEQUENCE: 15

Arg Arg Arg His Ile Val Arg Lys Arg Thr Leu Arg Arg Leu Leu Gln
1               5                   10                  15

Glu Arg Glu Leu Val Glu Pro Leu Thr Pro Ser Gly Glu Ala Pro Asn
```

```
               20                  25                  30

Gln Ala Leu
        35

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Arg His Ile Val Arg Lys Arg
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg His Ile Val Arg Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Arg His Ile Val Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Arg His Ile Val
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Arg His Ile
1               5

<210> SEQ ID NO 21
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Arg Arg Arg His
1

<210> SEQ ID NO 22
<211> LENGTH: 24
<212> TYPE: PRT
<213> ORGANISM: Homo sapiens

<400> SEQUENCE: 22

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 23
<211> LENGTH: 22
<212> TYPE: PRT
<213> ORGANISM: Homo sapiens

<400> SEQUENCE: 23

Met Leu Leu Leu Val Thr Ser Leu Leu Cys Glu Leu Pro His Pro
1               5                   10                  15

Ala Phe Leu Leu Ile Pro
            20

<210> SEQ ID NO 24
<211> LENGTH: 20
<212> TYPE: PRT
<213> ORGANISM: Homo sapiens

<400> SEQUENCE: 24

Met Val Leu Gln Thr Gln Val Phe Ile Ser Leu Leu Leu Trp Ile Ser
1               5                   10                  15

Gly Ala Tyr Gly
            20

<210> SEQ ID NO 25
<211> LENGTH: 16
<212> TYPE: PRT
<213> ORGANISM: Homo sapiens

<400> SEQUENCE: 25

Met Pro Leu Leu Leu Leu Leu Pro Leu Leu Trp Ala Gly Ala Leu Ala
1               5                   10                  15

<210> SEQ ID NO 26
<211> LENGTH: 335
<212> TYPE: PRT
<213> ORGANISM: Homo sapiens

<400> SEQUENCE: 26

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45
```

Thr His Thr Pro Pro Leu Asp Pro Gln Glu Leu Asp Ile Leu Lys Thr
 50                  55                  60

Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 27
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Lys Val Cys Asn Gly Ile Gly Ile Gly Glu Phe Lys Asp Ser Leu
 1               5                  10                  15

Ser Ile Asn Ala Thr Asn Ile Lys His Phe Lys Asn Cys Thr Ser Ile
                 20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
 50                  55                  60

Val Lys Glu Ile Thr Gly Phe Leu Leu Ile Gln Ala Trp Pro Glu Asn

Arg Thr Asp Leu His Ala Phe Glu Asn Leu Glu Ile Ile Arg Gly Arg
                    85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
        130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
                180                 185                 190

Gly Gly Pro Ser Ile Ala Thr Gly Met Val Gly Ala Leu Leu Leu Leu
            195                 200                 205

Leu Val Val Ala Leu Gly Ile Gly Leu Phe Met
    210                 215

<210> SEQ ID NO 28
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                    85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
        130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Thr Gly Ser Gly Trp
                165                 170                 175

Gly Pro Glu Pro Gly Gly Ser Pro Ser Ile Ala Thr Gly Met Val
            180                 185                 190

Gly Ala Leu Leu Leu Leu Val Val Ala Leu Gly Ile Gly Leu Phe
        195                 200                 205

Met

<210> SEQ ID NO 29
<211> LENGTH: 360
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 29

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met Arg Arg Arg
            355                 360

<210> SEQ ID NO 30
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
        50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met Arg Arg Arg His Ile Val Arg Lys Arg
        355                 360                 365

<210> SEQ ID NO 31
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly

```
                340               345                350
Ile Gly Leu Phe Met Arg Arg Arg Ser Gly Gly Gly Ser Gly Gly
            355                360                365

Gly Gly Ser
    370

<210> SEQ ID NO 32
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile
                20                  25                  30

Glu Phe Lys Asp Ser Leu Ser Ile Asn Ala Thr Asn Ile Lys His Phe
                35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
                115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
                180                 185                 190

Gln Val Cys His Ala Leu Cys Ser Pro Glu Gly Cys Trp Gly Pro Glu
                195                 200                 205

Pro Arg Asp Cys Val Ser Cys Arg Asn Val Ser Arg Gly Arg Glu Cys
                210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
                260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320
```

```
Gly Leu Glu Gly Cys Pro Thr Asn Gly Pro Lys Ile Pro Ser Ile Ala
            325                 330                 335

Thr Gly Met Val Gly Ala Leu Leu Leu Leu Val Val Ala Leu Gly
        340                 345                 350

Ile Gly Leu Phe Met Ser Gly Gly Gly Ser Gly Gly Gly Ser
        355                 360                 365
```

<210> SEQ ID NO 33
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Gly Gly Pro Ser Ile Ala Thr Gly Met Val
    210                 215                 220

Gly Ala Leu Leu Leu Leu Val Val Ala Leu Gly Ile Gly Leu Phe
225                 230                 235                 240

Met Arg Arg Arg
```

<210> SEQ ID NO 34
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Leu Leu Leu Val Thr Ser Leu Leu Leu Cys Glu Leu Pro His Pro
```

```
                1               5                    10                   15
            Ala Phe Leu Leu Ile Pro Arg Lys Val Cys Asn Gly Ile Gly Ile Gly
                            20                  25                  30

Glu Phe Lys Asp Ser Leu Ser Ile Asn Ala Thr Asn Ile Lys His Phe
                            35                  40                  45

Lys Asn Cys Thr Ser Ile Ser Gly Asp Leu His Ile Leu Pro Val Ala
                50                      55                  60

Phe Arg Gly Asp Ser Phe Thr His Thr Pro Pro Leu Asp Pro Gln Glu
            65                      70                  75                  80

Leu Asp Ile Leu Lys Thr Val Lys Glu Ile Thr Gly Phe Leu Leu Ile
                                85                  90                  95

Gln Ala Trp Pro Glu Asn Arg Thr Asp Leu His Ala Phe Glu Asn Leu
                            100                 105                 110

Glu Ile Ile Arg Gly Arg Thr Lys Gln His Gly Gln Phe Ser Leu Ala
                            115                 120                 125

Val Val Ser Leu Asn Ile Thr Ser Leu Gly Leu Arg Ser Leu Lys Glu
                130                     135                 140

Ile Ser Asp Gly Asp Val Ile Ile Ser Gly Asn Lys Asn Leu Cys Tyr
            145                     150                 155                 160

Ala Asn Thr Ile Asn Trp Lys Lys Leu Phe Gly Thr Ser Gly Gln Lys
                            165                 170                 175

Thr Lys Ile Ile Ser Asn Arg Gly Glu Asn Ser Cys Lys Ala Thr Gly
                            180                 185                 190

Gln Val Cys His Ala Leu Cys Ser Pro Glu Gly Cys Trp Gly Pro Glu
                            195                 200                 205

Pro Arg Asp Cys Val Ser Gly Gly Pro Ser Ile Ala Thr Gly Met Val
                210                     215                 220

Gly Ala Leu Leu Leu Leu Leu Val Val Ala Leu Gly Ile Gly Leu Phe
            225                     230                 235                 240

Met Arg Arg Arg His Ile Val Arg Lys Arg
                            245                 250

<210> SEQ ID NO 35
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Leu Leu Leu Val Thr Ser Leu Leu Leu Cys Glu Leu Pro His Pro
            1               5                   10                  15

Ala Phe Leu Leu Ile Pro Arg Lys Val Cys Asn Gly Ile Gly Ile Gly
                            20                  25                  30

Glu Phe Lys Asp Ser Leu Ser Ile Asn Ala Thr Asn Ile Lys His Phe
                            35                  40                  45

Lys Asn Cys Thr Ser Ile Ser Gly Asp Leu His Ile Leu Pro Val Ala
                50                      55                  60

Phe Arg Gly Asp Ser Phe Thr His Thr Pro Pro Leu Asp Pro Gln Glu
            65                      70                  75                  80

Leu Asp Ile Leu Lys Thr Val Lys Glu Ile Thr Gly Phe Leu Leu Ile
                                85                  90                  95

Gln Ala Trp Pro Glu Asn Arg Thr Asp Leu His Ala Phe Glu Asn Leu
                            100                 105                 110
```

```
Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Gly Gly Pro Ser Ile Ala Thr Gly Met Val
210                 215                 220

Gly Ala Leu Leu Leu Leu Leu Val Val Ala Leu Gly Ile Gly Leu Phe
225                 230                 235                 240

Met Arg Arg Arg Ser Gly Gly Gly Gly Ser Gly Gly Gly Gly Ser
                245                 250                 255

<210> SEQ ID NO 36
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Gly Gly Pro Ser Ile Ala Thr Gly Met Val
210                 215                 220
```

```
Gly Ala Leu Leu Leu Leu Val Val Ala Leu Gly Ile Gly Leu Phe
225                 230                 235                 240

Met Ser Gly Gly Gly Ser Gly Gly Gly Ser
                245                 250

<210> SEQ ID NO 37
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Thr Gly Ser Gly Trp Gly Pro Glu Pro Gly Gly Ser Pro Ser
        195                 200                 205

Ile Ala Thr Gly Met Val Gly Ala Leu Leu Leu Leu Val Val Ala
    210                 215                 220

Leu Gly Ile Gly Leu Phe Met Arg Arg Arg
225                 230

<210> SEQ ID NO 38
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
                20                  25                  30
```

```
Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
 50                  55                  60

Phe Arg Gly Asp Ser Phe Thr His Thr Pro Pro Leu Asp Pro Gln Glu
 65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
                115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
                180                 185                 190

Gln Thr Gly Ser Gly Trp Gly Pro Glu Pro Gly Gly Ser Pro Ser
                195                 200                 205

Ile Ala Thr Gly Met Val Gly Ala Leu Leu Leu Leu Leu Val Val Ala
                210                 215                 220

Leu Gly Ile Gly Leu Phe Met Arg Arg Arg His Ile Val Arg Lys Arg
225                 230                 235                 240

<210> SEQ ID NO 39
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Leu Leu Leu Val Thr Ser Leu Leu Cys Glu Leu Pro His Pro
 1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
 50                  55                  60

Phe Arg Gly Asp Ser Phe Thr His Thr Pro Pro Leu Asp Pro Gln Glu
 65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
                115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
```

```
                    145                 150                 155                 160
Ala Asn Thr Ile Asn Trp Lys Lys Leu Phe Gly Thr Ser Gly Gln Lys
                    165                 170                 175

Thr Lys Ile Ile Ser Asn Arg Gly Glu Asn Ser Cys Lys Ala Thr Gly
                    180                 185                 190

Gln Thr Gly Ser Gly Trp Gly Pro Glu Pro Gly Gly Ser Pro Ser
                    195                 200                 205

Ile Ala Thr Gly Met Val Gly Ala Leu Leu Leu Leu Val Val Ala
                    210                 215                 220

Leu Gly Ile Gly Leu Phe Met Arg Arg Arg Ser Gly Gly Gly Ser
225                 230                 235                 240

Gly Gly Gly Gly Ser
                    245

<210> SEQ ID NO 40
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Leu Leu Leu Val Thr Ser Leu Leu Cys Glu Leu Pro His Pro
1                   5                   10                  15

Ala Phe Leu Leu Ile Pro Arg Lys Val Cys Asn Gly Ile Gly Ile Gly
                    20                  25                  30

Glu Phe Lys Asp Ser Leu Ser Ile Asn Ala Thr Asn Ile Lys His Phe
                    35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                    85                  90                  95

Gln Ala Trp Pro Glu Asn Arg Thr Asp Leu His Ala Phe Glu Asn Leu
                    100                 105                 110

Glu Ile Ile Arg Gly Arg Thr Lys Gln His Gly Gln Phe Ser Leu Ala
                    115                 120                 125

Val Val Ser Leu Asn Ile Thr Ser Leu Gly Leu Arg Ser Leu Lys Glu
                    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                    165                 170                 175

Thr Lys Ile Ile Ser Asn Arg Gly Glu Asn Ser Cys Lys Ala Thr Gly
                    180                 185                 190

Gln Thr Gly Ser Gly Trp Gly Pro Glu Pro Gly Gly Ser Pro Ser
                    195                 200                 205

Ile Ala Thr Gly Met Val Gly Ala Leu Leu Leu Leu Val Val Ala
                    210                 215                 220

Leu Gly Ile Gly Leu Phe Met Ser Gly Gly Gly Ser Gly Gly Gly
225                 230                 235                 240

Gly Ser
```

```
<210> SEQ ID NO 41
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Glu Ala Arg Lys Ala Ile Ala Arg Val Lys Arg Glu Ser Lys Arg
1               5                   10                  15

Ile Val Glu Asp Ala Glu Arg Leu Ile Arg Glu Ala Ala Ala Ala Ser
            20                  25                  30

Glu Lys Ile Ser Arg Glu Ala Glu Arg Leu Ile
        35                  40

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Gly Gly Ser Gly Gly Gly Gly Ser
1               5                   10

<210> SEQ ID NO 43
<211> LENGTH: 58
<212> TYPE: PRT
<213> ORGANISM: Homo sapiens

<400> SEQUENCE: 43

Ile Ala Thr Gly Met Val Gly Ala Leu Leu Leu Leu Leu Val Val Ala
1               5                   10                  15

Leu Gly Ile Gly Leu Phe Met Arg Arg Arg His Ile Val Arg Lys Arg
            20                  25                  30

Thr Leu Arg Arg Leu Leu Gln Glu Arg Glu Leu Val Glu Pro Leu Thr
        35                  40                  45

Pro Ser Gly Glu Ala Pro Asn Gln Ala Leu
    50                  55

<210> SEQ ID NO 44
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ala Thr Gly Met Val Gly Ala Leu Leu Leu Leu Leu Val Val Ala
1               5                   10                  15

Leu Gly Ile Gly Leu Phe Met Arg Arg Arg
            20                  25

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 45

Ile Ala Thr Gly Met Val Gly Ala Leu Leu Leu Leu Val Val Ala
1               5                   10                  15

Leu Gly Ile Gly Leu Phe Met Arg Arg Arg His Ile Val Arg Lys Arg
                20                  25                  30

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ile Ala Thr Gly Met Val Gly Ala Leu Leu Leu Leu Val Val Ala
1               5                   10                  15

Leu Gly Ile Gly Leu Phe Met Arg Arg Arg Ser Gly Gly Gly Ser
                20                  25                  30

Gly Gly Gly Gly Ser
        35

<210> SEQ ID NO 47
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ile Ala Thr Gly Met Val Gly Ala Leu Leu Leu Leu Val Val Ala
1               5                   10                  15

Leu Gly Ile Gly Leu Phe Met Ser Gly Gly Gly Ser Gly Gly
                20                  25                  30

Gly Ser
```